United States Patent [19]

Girard et al.

[11] Patent Number: 5,308,852

[45] Date of Patent: May 3, 1994

[54] HETEROARYLNAPHTHALENES AS INHIBITORS OF LEUKOTRIENE BIOSYNTHESIS

[75] Inventors: Yves Girard, Ile Bizard; Daniel Delorme, St. Lazare; Rejean Fortin, Montreal-Nord; Daniel Dube, St. Lazare; Pierre Hamel, Vimont; Carol Lepine, Vimont Laval; Yves Ducharme, Montreal, all of Canada

[73] Assignee: Merck Frosst Canada, Inc., Kirkland, Canada

[21] Appl. No.: 936,807

[22] Filed: Aug. 27, 1992

Related U.S. Application Data

[63] Continuation-in-part of Ser. No. 906,067, Jun. 29, 1992, abandoned.

[51] Int. Cl.$^5$ .............. A61K 31/445; A61K 31/335; C07D 309/10; C07D 309/02
[52] U.S. Cl. ..................... 514/336; 514/338; 514/365; 514/444; 514/450; 514/451; 514/460; 546/270; 546/283; 546/284; 546/268; 548/203; 549/60; 549/355; 549/414; 549/420; 549/423
[58] Field of Search ........... 546/270, 283, 284, 268; 548/203; 549/60, 355, 414, 420, 423; 514/336, 338, 365, 444, 450, 451, 460

[56] References Cited

U.S. PATENT DOCUMENTS 4,486,445  12/1984  Patel et al. .................. 424/279
4,937,373   6/1990  Carson et al. ................. 560/56

FOREIGN PATENT DOCUMENTS 0188248  7/1986  European Pat. Off. .
0351194  1/1990  European Pat. Off. .
0372385  6/1990  European Pat. Off. .
0375368  6/1990  European Pat. Off. .
0375404  6/1990  European Pat. Off. .
0375452  6/1990  European Pat. Off. .
0380982  8/1990  European Pat. Off. .
0381375  8/1990  European Pat. Off. .
0385662  9/1990  European Pat. Off. .
0385663  9/1990  European Pat. Off. .
0385679  9/1990  European Pat. Off. .
0385680  9/1990  European Pat. Off. .
0409413  1/1991  European Pat. Off. .
0462812  12/1991 European Pat. Off. .
0462830  12/1991 European Pat. Off. .

OTHER PUBLICATIONS

The Merck Index, 11th ed., 5154, pp. 829 (1989).

*Primary Examiner*—Marianne M. Cintins
*Assistant Examiner*—Michael B. Hydorn
*Attorney, Agent, or Firm*—Mark R. Daniel; Joseph F. DiPrima

[57] ABSTRACT

Compounds having the formula I:

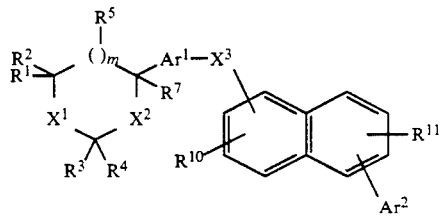

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection and in preventing the formation of atherosclerotic plaques.

11 Claims, No Drawings

5,308,852

HETEROARYLNAPHTHALENES AS INHIBITORS OF LEUKOTRIENE BIOSYNTHESIS

CROSS-REFERENCE

This is a CIP of Ser. No. 07/906,067, Jun. 29, 1992, now abandoned.

BACKGROUND OF THE INVENTION AND PRIOR ART

The leukotrienes constitute a group of locally acting hormones, produced in living systems from arachidonic acid. The major leukotrienes are Leukotriene $B_4$ (abbreviated at $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

European patent application 375,404 (Jun. 27, 1990) describes certain naphthalene-containing heterocyclic ethers of structure A which are inhibitors of the enzyme 5-lipoxygenase. EP 375,452 (Jun. 27, 1990) describes naphthalene-containing hydrocarbon ethers of structure B which are reported to possess the same activity. EP 462,830 (Dec. 27, 1991) describes bicyclic heterocycle-containing hydrocarbon ethers of structure C which are reported to possess the same activity. All these series of prior art compounds differ significantly from the present invention in that they lack the aryl substituent of the present compounds.

A series of natural products known as the justicidines are referred to in the Merck Index, 11th edition, 1989, no. 5154. The justicidins differ considerably from the present compounds in that they lack the large pyranylphenyl group.

$Ar^1-A^1-O-Ar^2-\underset{\underset{R^3}{|}}{\overset{\overset{OR^1}{|}}{C}}-R^2$  A EP 375,404 ICI-Pharma $Ar^1-A^1-O-Ar^2-\underset{\underset{R^3}{|}}{\overset{\overset{OR^1}{|}}{C}}-R^2$  B EP 375,452 ICI-Pharma $Ar^1-A^1-O-Ar^2-\underset{\underset{R^3}{|}}{\overset{\overset{R^1}{|}}{C}}-R^2$  C EP 462,830 ICI-Pharma Justicidins. Merck Index No. 5154

SUMMARY OF THE INVENTION

The present invention relates to heteroarylnaphthalenes having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection and in preventing the formation of atherosclerotic plaques.

DETAILED DESCRIPTION OF THE INVENTION

The compounds of the present invention may be represented by the following formula I:

wherein:
$R^1$ and $R^5$ is each independently H, OH, lower alkyl, or lower alkoxy;
$R^2$ is H, lower alkyl, or together with $R^1$ forms a double bonded oxygen (=O);
$R^3$ is H, lower alkyl, hydroxy lower alkyl, or lower alkoxy lower alkyl, or $R^1$ and $R^3$ may join to form a carbon bridge of 2 or 3 carbon atoms or a mono-oxa carbon bridge of 1 or 2 carbon atoms, said bridge optionally containing a double bond;
$R^4$ is H or lower alkyl;
$R^6$ is H or lower alkyl, or two $R^6$ groups attached to the same carbon may form a saturated ring of 3 to 8 members;
$R^7$ is H, OH, lower alkyl, lower alkoxy, lower alkylthio, lower alkylcarbonyloxy, or $O-R^{15}$;
$R^8$ is H, halogen, lower alkyl, hydroxy, lower alkoxy, $CF_3$, CN, or $COR^{13}$;
$R^9$ is H, lower alkyl, lower alkoxy, hydroxy lower alkyl, lower alkoxy lower alkyl, lower alkylthio lower alkyl, $(R^8)_2$-phenylthio lower alkyl, lower alkylthio lower alkylcarbonyl, CN, $O_2$, $CF_3$, $N_3$, $N(R^{12})_2$, $NR^{12}COR^{13}$, $NR^{12}CON(R^{12})_2$, $SR^{14}$, $S(O)R^{14}$, $S(O)_2R^{14}$, $S(O)_2N(R^{12})_2$, $COR^{13}$, $CON(R^{12})_2$, $CO_2R^{13}$, $C(R^{13})_2OC(R^{13})_2$-$CO_2R^{13}$, $C(R^{13})_2CN$, or halogen;

$R^{10}$ and $R^{11}$ is each independently H, lower alkyl, lower alkoxy, hydroxy lower alkyl, lower alkoxy, lower alkyl, lower alkylthio lower alkyl, $(R^8)_2$-phenylthio lower alkyl, lower alkylthio lower alkylcarbonyl, CN, $NO_2$, $CF_3$, $N_3$, $N(R^{16})_2$, $NR^{16}COR^{13}$, $NR^{16}CON(R^{16})_2$, $SR^{14}$, $S(O)R^{14}$, $S(O)_2R^{14}$, $S(O)_2(R^{16})_2$, $COR^{13}$, $CON(R^{16})_2$, $CO_2R^{13}$, $C(R^{13})_2OC(CR^{13})_2$-$CO_2R^{13}$, $C(R^{13})_2CN$, halogen, $C(R^{13})_2R^{16}COR^{13}$, or $C(R^{13})_2R^{16}CON(R^{13})_2$;

$R^{12}$ is H or lower alkyl, or two $R^{12}$ groups attached to the same nitrogen may form a saturated ring of 5 or 6 members, optionally containing a second heteroatom chosen from O, S or $R^4$;

$R^{13}$ is H or lower alkyl;

$R^{14}$ is lower alkyl, $CF_3$, or phenyl-$(R^8)_2$;

$R^{15}$ is carboxy lower alkylcarbonyl, pyridylcarbonyl, hydroxy lower alkylcarbonyl, polyoxa lower alkylcarbonyl, a functionalized or unfunctionalized derivative of a standard amino acid, or a benzoyl group substituted by $CH_2N(R^{12})_2$;

$R^{16}$ is H, lower alkyl, or $OR^{13}$;

$X^1$ is O, S, S(O), $S(O)_2$, or $C(R^6)_2$;

$X^2$ is O, S, $C(R^6)_2$, or a bond;

$X^3$ is $C(R^6)_2O$ or $OC(R^6)_2$;

$Ar^1$ is arylene-$(R^8)_2$, wherein arylene is a 5-membered aromatic ring wherein one carbon atom is replaced by O or S and 0–2 carbon atoms are replaced by N; a 5-membered aromatic ring wherein 1–3 carbon atoms are replaced by N; a 6-membered aromatic ring wherein 0–3 carbon atoms are replaced by N; 2- or 4-pyranone; or 2- or 4-pyridinone;

$Ar^2$ is aryl-$(R^9)_2$ wherein aryl is a 5-membered aromatic ring wherein one carbon atom is replaced by O or S and 0–3 carbon atoms are replaced by ; a 5-membered aromatic ring wherein 1–4 carbon atoms are replaced by N; a 6-membered aromatic ring wherein 0–3 carbon atoms are replaced by N; 2- or 4-pyranone; 2- or 4-pyridinone; or a bicyclic 8-, 9-, or 10-membered aromatic ring wherein 0–2 carbon atoms are replaced by either O or S or a combination thereof and 0–3 carbon atoms are replaced by N; with the proviso that $Ar^2$ is not phenyl when $X^3$ is $OC(R^6)_2$, $Ar^1$ is a 5-membered aromatic ring, and $R^7$ is lower alkoxy; with the further proviso that $Ar^2$ is not phenyl when $X^3$ is $OC(R^6)_2$, $Ar^1$ is a 6-membered aromatic ring, and $R^7$ is H, lower alkyl, or lower alkylthio;

$Ar^2$ is attached to either ring of the naphthalene ring system;

m is 0 or 1;

p is 0 to 6; and q is 1 or 2;

or a pharmaceutically acceptable salt thereof.

A preferred embodiment of the present invention is represented by Formula Ia:

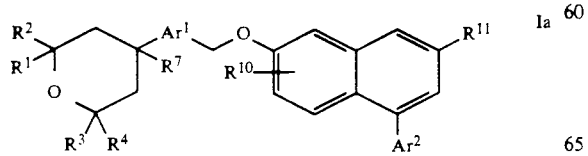

wherein:

$R^{10}$ is H, lower alkyl, or halogen;

and the remaining substituents are as defined for Formula I.

Another preferred embodiment of the present invention is represented by Formula Ib:

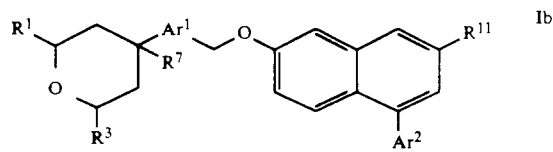

wherein:

$R^1$ and $R^3$ is each independently H or $CH_3$ or together are —$CH_2O$— or —$OCH_2$—;

$R^7$ is OH or $OCH_3$;

$Ar^1$ is Phe, 5,3-Pye, 2,4-Tze, 6,2-Pye, 4,2-Pye, or 2,4-Pye;

$Ar^2$ is Ph, 3-Fu, 2-Th, 3-Th, 2-Tz, 5Tz, 5-Pym, or 5-Tet;

$R^{11}$ is $CO_2CH_3$, $C(OH)(CH_3)_2$, $CH(OH)CH_3$, $CH(OCH_3)CH_3$, $CH_2CH_3$, $CO(CH_2)_3CH_3$, $CON(CH_3)_2$, $CH_2SC_6H_5$, $CH_2SCH_3$, $CH_2CN$, $COCH_2SCH_3$, $CH_2OCH_2CO_2CH_3$, CN, CHO, H, $COCH_3$, or $CH_2N(OH)COCH_3$.

Another preferred embodiment of the present invention is represented by Formula Ic.

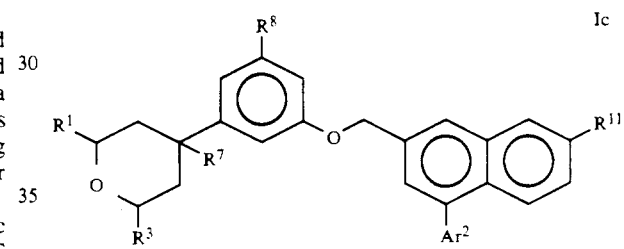

wherein:

$R^1$ and $R^3$ is each H or together are —$CH_2O$— or —$OCH_2$—;

$R^7$ is OH or $OCH_3$;

$R^8$ is H or F;

$Ar^2$ is 3-Fu, 3-Th, or Ph;

$R^{11}$ is $CO_2CH_3$ or CN.

Definitions

The following abbreviations have the indicated meanings:

| | |
|---|---|
| Ac = | acetyl |
| Bn = | benzyl |
| i-Pr = | isopropyl |
| n-Pr = | normal propyl |
| n-Bu = | normal butyl |
| i-Bu = | isobutyl |
| s-Bu = | secondary butyl |
| t-Bu = | tertiary butyl |
| Et = | ethyl |
| Fu = | 2- or 3-furyl |
| Me = | methyl |
| Ph = | phenyl |
| Py = | 2-, 3-, or 4-pyridyl |
| Th = | 2-, or 3-thienyl |
| Tz = | 2-, 4-, or 5-thiazolyl |
| Tf = | trifluoromethanesulfonyl |
| AIBN = | azoisobtyronitrile |
| Bu$_4$NF = | tetra-n-butylammonium fluoride |
| CH$_2$N$_2$ = | diazomethane |
| CSA = | camphor sulfonic acid |
| DCC = | 1,3-dicyclohexylcarbodiimide |
| DDQ = | 2,3-dichloro-5,6-dicyano-1,4-benzo- |

-continued

| | | |
|---|---|---|
| | | quinone |
| DHP | = | 3,4-dihydro-2H-pyran |
| DIBAL-H | = | diisobutylaluminum hydride |
| DIPHOS | = | 1,2-Bis(diphenylphosphino)ethane |
| DMAP | = | 4-dimethylaminopyridine |
| DMF | = | N,N-dimethylformamide |
| DMSO | = | dimethylsulfoxide |
| $Et_3N$ | = | triethylamine |
| LDA | = | lithium diisopropylamide |
| Ms | = | methanesulfonyl = mesyl |
| Phe | = | benzenediyl |
| Pye | = | pyridindiyl |
| Pym | = | pyrimidinyl |
| PCC | = | pyridinium chlorochromate |
| RIA | = | radioimmuno assay |
| r.t. | = | room temperature |
| Super-Hydride | = | lithium triethylborohydride |
| t-BOC | = | tertiary butyloxy carbonyl |
| Tet | = | 1H (or 2H)-tetrazol-5-yl |
| TFA | = | trifluoroacetic acid |
| TFAA | = | trifluoroacetic anhydride |
| THF | = | tetrahydrofuran |
| TMSCl | = | chlorotrimethylsilane |
| Ts | = | p-toluenesulfonyl = tosyl |
| Tze | = | thiazoldiyl |

Alkyl is intended to include linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

The term "lower alkyl" means those alkyl groups of from 1 to 7 carbon atoms. Examples of lower alkyl groups include methyl, ethyl, propyl, isopropyl, butyl, s- and t-butyl, pentyl, hexyl, heptyl, and the like.

The term "lower alkoxy" means those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, cyclohexylacetyl, etc. By way of illustration, the 2-methylbutanoyl group signifies $-C(O)CH(CH_3)CH_2CH_3$.

"Carboxy lower alkylcarbonyl" means the group $-C(O)(CH_2)_pCO_2H$, wherein p is 0 to 6.

"Hydroxy lower alkylcarbonyl" means the group $-C(O)(CH_2)_p-OH$, wherein p is 0–6.

"Hydroxy lower alkyl" means a lower alkyl group carrying a hydroxy group; e.g., $-CH_2CH(OH)CH_2CH_3$.

"Lower alkoxy lower alkyl" means a lower alkyl group carrying a lower alkoxy group; e.g., $-CH_2CH_2OCH_3$.

"Lower alkylthio" means alkylthio groups of from 1 to 7 carbon atoms of a straight, branched or cyclic configuration. Examples of lower alkylthio groups include methylthio, ethylthio, isopropylthio, cyclobutylthio, and the like.

"Lower alkylthio lower alkyl" means a lower alkyl group carrying a lower alkylthio group; e.g., $-CH_2CH_2S-c-Pr$.

"Lower alkylthio lower alkylcarbonyl" means a lower alkylcarbonyl group carrying a lower alkylthio group; e.g., $-COCH_2SCH_2CH_3$.

"$(R^8)_2$-phenylthio lower alkyl" means a lower alkyl group carrying phenylthio group which in turn carries two $R^8$ substituents; e.g., $-CH_2CH_2S-Ph-4-CN$.

The term "standard amino acid" means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, and valine. (See F. H. C. Crick, Symposium of the Society of Experimental Biology, 1958 (12), p. 140). Examples of $R^{15}$ derived from standard amino acids are $C(O)(CH_2)_q-N(R^{12})_2$, $-C(O)CH(NH-t-BOC)(CH_2)_qCO_2H$, and $-C(O)CH(N(R^{12})_2)(CH_2)_qCO_2R^{13}$.

Examples of saturated rings which may be formed by two $R^{12}$ groups attached to the same nitrogen are pyrrolidine, piperidine, morpholine, thiamorpholine, piperazine, and N-lower alkyl piperazine.

Examples of "arylene" are furan, thiophene, oxazole, thiazole, 1,3,4-oxadiazole, 1,3,4-thiadiazole, 1,2,5-oxadiazole, 1,2,5-thiadiazole, pyrrole, imidazole, 1,3,4-triazole, benzene, pyridine, pyrazine, pyrimidine, pyridazine, 1,2,3-triazine, 1,2,4-triazine, and 1,3,5-triazine.

Examples of "aryl" are furan, thiophene, oxazole, thiazole, isoxazole, isothiazole, 1,3,4-oxadiazole, 1,3,4-thiadiazole, 1,2,5-oxadiazole, 1,2,5-thiadiazole, pyrrole, pyrazole, imidazole, 1,3,4-triazole, tetrazole, benzene, pyridine, pyrazine, pyrimidine, pyridazine, 1,2,3-triazine, 1,2,4-triazine, 1,3,5-triazine, thieno[2,3-b]furan, thieno[3,2-b]pyrrole, indole, benzofuran, benzothiophene, benzimidazole, benzoxazole, benzothiazole, benzo[2,1,3]thiadiazole, furano[3,2-b]pyridine, naphthalene, quinoline, isoquinoline, quinoxaline, quinazoline, cinnoline, phthalazine, 1,8-naphthyridine, and the like.

Halogen includes F, Cl, Br, and I.

It is intended that the definitions of any substituent (e.g., $R^6$, $R^{12}$, etc.) in a particular molecule be independent of its definitions elsewhere in the molecule. Thus, $C(R^6)_2$ represents $CH_2$, $CHCH_3$, $C(CH_3)_2$, etc.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) multiple sclerosis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding &uture damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200; and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |

| -continued | |
|---|---|
| Trichlorofluoromethane, NF | 4.025 gm |
| Dichlorodifluoromethane, NF | 12.15 gm |

Combinations with other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives,
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH3)COOH or —CH2CH2COOH group (which optionally can be in the form of a pharmaceutically acceptable salt group, e.g., —CH(CH3)COO$^-$Na$^+$ or —CH2CH2COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH2COOH group (which optionally can be in the form of a pharmaceutically acceptable salt group, e.g. —CH2COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

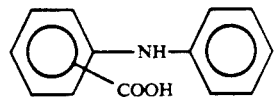

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

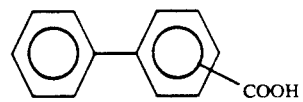

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

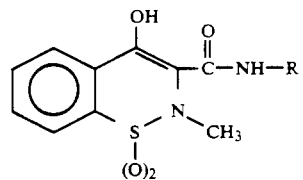

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see, e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods. Temperatures are in degrees Celsius. The substituents are the same as in Formula I except where defined otherwise.

Scheme I

One method for the synthesis of naphthol intermediates (Method A) is outlined in Scheme I. A 4-aryl-4-oxobutanoic acid III, on heating with acetic anhydride and NaOAc, is transformed into the corresponding enol lactone, which condenses in situ with an aldehyde II to afford lactone IV. Upon refluxing in a mixture of glacial AcOH and concentrated HCl, transformation to naphthoic acid V occurs. Heating with pyridine hydrochloride then affords the free naphthol VI.

Scheme II

In the preparation of naphthol intermediates via Method B, an aldehyde of type II is initially condensed with a succinic acid diester VII, in the presence of an alkoxide such as LiOMe, with the corresponding alcohol (MeOH) as solvent, to afford a 3-carbalkoxy-4-phenyl butenoic acid VIII. This material, on treatment with TFAA in the presence of NaOAc in a solvent such as $CH_2Cl_2$, cyclizes to the naphthoic ester IX. The trifluoroacetyl group is cleaved by treatment with an inorganic base such as $K_2CO_3$ in a polar solvent such as MeOH, to afford phenol X which is transformed, using trifluoromethane sulfonic anhydride, in the presence of an amine such as $Et_3N$, in a neutral solvent such as $CH_2Cl_2$, to the corresponding triflate XI. Alternatively, treatment of VIII with $Tf_2O$, with or without a suitable solvent such as $CH_2Cl_2$, affords triflate XI directly. Cross coupling of this material with an aryl lithium species (resulting from reaction of an aryl halide (Br or I) with an alkyl lithium such as n-BuLi in a mixture of THF-hexane), in the presence of trimethyl borate and catalyzed by a Pd(O) species such as $(Ph_3P)_4Pd$, in a mixture of THF and water as solvent, affords the 1-aryl-3-naphthoic ester XII. Where $R_1$=methyl, this material, on heating with pyridine hydrochloride, affords naphthol acid VI which is esterified, such as by treatment with $CH_2N_2$, to the corresponding methyl ester XV ($R_2$=Me). Where $R_1$=benzyl, the benzyl group is removed by heating in a mixture of TFA and thioanisole, to afford naphthol ester XV. Alternatively, alkoxy naphthoic ester XII can be transformed to the corresponding nitrile XIII by initial reaction with dimethyl aluminum amide, in a high-boiling solvent such as toluene, producing an intermediate amide which is converted to the nitrile using a dehydrating agent such as TFAA. Subsequent transformation to the phenol XIV is effected using, whether $R_1$ is methyl or benzyl, the appropriate method as described above for the preparation of naphthol ester XV.

Scheme III

An alternative method for the preparation of naphthols of type VI, XIV, and XV is outlined in Scheme III. The intermediate 3-carbalkoxy-4-phenyl butenoic acid VIII from Scheme II is reduced, by hydrogenation over a noble metal catalyst such as palladium, in a solvent such as acetic acid, to the corresponding butanoic acid XVI. This material is cyclized, using a dehydrating agent such as TFAA in the presence of NaOAc, to the tetralone ester XVII. Condensation of this material with an aryl magnesium halide or an aryl lithium species, in an ethereal solvent such as diethyl ether, affords an intermediate tertiary alcohol and/or the corresponding lactone; the crude product, on refluxing in an inert solvent such as benzene in the presence of a strong acid such as CSA, affords the dihydro naphthoate XVIII which is dehydrogenated, using an oxidant such as DDQ in an inert solvent such as benzene, to the naphthoate XII. Transformation to the naphthols VI, XIV, and XV is effected as described in Scheme II.

Scheme IV

This scheme outlines the preparation of several other types of naphthol intermediates. The 3-carboxy-6-naphthol VI from Scheme 1 is decarboxylated by heating with metallic copper in a high-boiling solvent such as quinoline, to afford naphthol XIX. Alternatively, coupling of VI with an alkyl lithium species, in an ethereal solvent such as diethyl ether, affords ketone derivatives XX, which can be reduced by hydrogenation over a noble metal catalyst such as palladium, to the corresponding alkyl analogs XXI. Esterification of naphthol acids VI, in an alcoholic solvent in the presence of an acid, such as gaseous HCl, leads to esters XXII. These esters can be converted to the corresponding amides XXIII, by reaction with an aluminum amide species in a solvent such as toluene. Esters XXII can be transformed, by the procedure described in Scheme II for the conversion of XII to XIII, to nitriles XIV. Conversion to aldehydes XXIV is achieved through the use of an aluminum hydride reagent, such as DIBAL-H, in an inert solvent such as toluene. Reduction of acid VI or ester XXII, using an aluminum hydride reagent such as DIBAL-H, in an ethereal solvent such as THF, produces alcohol XXV. This material is converted to the corresponding halide XXVI through the action of triphenyl phosphine in a halogenated solvent such as $CCl_4$ or $CBrCl_3$. Coupling of this halide with a thioalkoxide, resulting from reaction of a thiol with a metal hydride such as NaH in a polar solvent such as DMF, generates sulfides XXVII.

Scheme V

The preparation of compounds of Formula I (wherein $X^3 = -C(R^6)_2O-$) is described in Scheme V. A first method requires coupling of a naphthol XXIX (prepared according to Schemes I–IV) with a benzylic halide or activated alcohol XXVIII (wherein $X = Cl$, Br, I, OMs, OTs) in a polar organic solvent such as DMF in the presence of an inorganic base such as $Cs_2CO_3$.

In an alternate procedure, naphthol XXIX is condensed with a benzylic alcohol XXVIII (wherein $X = OH$) in the presence of a phosphine such as $Ph_3P$ and a azodicarboxylate diester, in a solvent such as THF, to afford Formula I compounds (wherein $X^3 = -C(R^6)_2O-$).

Scheme VI

The syntheses of several types of Formula I compounds are outlined in Scheme VI. An ester of type IA (a sub-group of I (wherein $X^3 = -C(R^6)_2O-$)) can be reduced, by treatment with an aluminum hydride reagent such as DIBAL-H, in a solvent such as a THF-toluene mixture, to the corresponding benzylic alcohol ID, which, on treatment with a metal hydride such as NaH in a solvent such as THF, with subsequent addition of an alkyl halide, ($R_2X$), is converted to the alkoxy methyl derivative IG.

A similar alkylation of ID using a halo acid or ester ($XC(R^{13})_2CO_2R^{13}$), in a polar solvent such as DMF in the presence of an inorganic base such as $Cs_2CO_3$, affords carbalkoxy methoxy methyl derivates of formula IH.

Esters IA can be hydrolyzed to the corresponding acids IB by reaction with an inorganic alkali metal hydroxide, such as LiOH, in a polar solvent, such as a mixture of THF, MeOH and $H_2O$, followed by acidification with an aqueous solution of a proton acid such as aq. HCl. An acid of type IB is transformed, via condensation with an alkyl lithium species, $R_2Li$, in an ethereal solvent such as $Et_2O$, to the corresponding ketone IC which on reduction with a hydride reagent such as $NaBH_4$, in a protic solvent such as ethanol, is converted to the secondary alcohol IF. In turn, this species can be alkylated, by treatment with a metal hydride such as NaH in a solvent such as THF, with subsequent addition of an alkyl halide, ($R_2X$), to the alkoxy derivative IJ. Compounds of formula IE are obtained by condensation of the ester IA with an alkyl Grignard or alkyl lithium species, $R_2Li$, in an ethereal solvent such as $Et_2O$.

Scheme VII

The synthesis of compounds of Formula I (wherein $X^3 = -OCH_2-$) is described in Scheme VII. The phenol XXIX may be converted to the triflate XXX by treatment with trifluoromethanesulfonic anhydride in the presence of an organic base such as pyridine in a solvent such as $CH_2Cl_2$. Subsequent treatment of XXX in a solvent such as DMSO/methanol with an organic base such as triethylamine, a phosphine such as 1,1'-bis(-diphenylphosphino)ferrocene and a palladium(II) salt such as palladium(II)acetate under an atmosphere of carbon monoxide will lead to the ester XXXI. The hydrolysis of the ester XXXI may be achieved using an inorganic base such as lithium hydroxide in water and the resulting acid XXXII may be reduced to the alcohol XXXIII by treatment with a chloroformate such as isopropyl chloroformate in the presence of an organic base such as triethylamine in an organic solvent such as THF, followed by addition of a reducing agent such as sodium borohydride in water. The alcohol XXXIII may be then converted to the halide XXXIV by treatment with triphenylphosphine, imidazole and $CBr_4$ in an organic solvent such as $CH_2Cl_2$. Coupling of halide XXXIV with the appropriate phenol XXXV in an organic solvent such as DMF using an inorganic base such as $K_2CO_3$ provides compounds of formula I (wherein $X^3 = -OCH_2-$) of the present invention.

Scheme VIII

The preparation of compounds of Formula I (wherein $R^7 = OR^{15}$) is outlined in Scheme VIII. The tertiary alcohol I (wherein $R^7 = OH$) can be converted to the acylated derivative I (wherein $R^7 = OR^{15}$) by treatment with the appropriate carboxylic acid in the presence of a dehydrating agent such as DCC and of an organic base such as DMAP in an organic solvent such as $CH_2Cl_2$. In the cases wherein the $R^{15}$ group contains an ester functionality, this ester can be selectively hydrolyzed under basic conditions. In the cases wherein the $R^{15}$ group contains an amine functionality bearing a protecting group such as t-Boc, this group can be cleaved under acidic conditions. In the cases where the $R^{15}$ group contains an alcohol functionality bearing a protecting group such as tert-butyldiphenylsilyl, this group can be cleaved by treatment with $Bu_4NF$.

Scheme IX

The intermediate naphthol XXXIX may be prepared from 2-bromo-5-benzyloxy benzaldehyde dimethylacetal XXXVI as outlined in Scheme IX. The bromo derivative XXXVI is converted to the alcohol XXXVII by treatment with a base such as n-butyl lithium in an organic solvent such as hexane followed by the addition of an aryl carboxaldehyde such as 3-furaldehyde in an organic solvent such as THF. The Diels-Alder reaction is achieved by heating the alcohol XXXVII in the presence of a Michael acceptor of type $CH_2=CH-E$ (wherein $E=CN$, $CO_2R^{13}$, $CON(R^{12})_2$, $NO_2$, $S(O)_2R^{14}$, $S(O)_2N(R^{12})_2$, or $COR^{13}$) in an organic solvent such as toluene, providing the nitrile compound XXXVIII. The debenzylation process to provide the naphthol intermediate XXXIX is described in Scheme II.

Scheme X

The naphthalene intermediate XLII may be prepared by using a naphthol such as XV or XXII where the phenol is converted to the trifluoromethane-sulfonate using trifluoromethanesulfonic anhydride in the presence of an amine such as $Et_3N$ in a neutral solvent such as $CH_2Cl_2$. Reduction of the ester XL using an aluminum hydride such as DiBAL-H, in an ethereal solvent such as THF, produces the alcohol XLI. Subsequent treatment of XLI in a solvent such as DMSO/methanol with an organic base such as triethylamine, a phosphine such as 1,1'-bis(diphenylphosphino)ferrocene and a palladium(II) salt such as palladium(II) acetate under an atmosphere of carbon moxoxide will lead to the naphthalene intermediate XLII.

Scheme XI

The preparation of the naphthol intermediate XLVI may be prepared starting from the corresponding naphthol XXII. The naphthol XXII is converted to the ester XLIV through the corresponding triflate XLIII using the same procedure as described in Scheme X. The ketoester XLIV is transformed to the corresponding acetate XLV via a Baeyer-Villager type reaction using an oxidant such as m-chloroperbenzoic acid in a refluxing organic solvent such as $CHCl_3$. The corresponding acetate XLV is then transformed to the naphthol intermediate XLVI by a base treatment such as $K_2CO_3$ in a protic solvent such as methanol.

Scheme XII

The naphthalene intermediate XLVII may be prepared as outlined in Scheme XII. The naphthol XXXIX (from Scheme IX) is transformed using the same strategy as outlined in Scheme X. Using the same starting material, the naphthol XXXIX is converted to the methyl ketone XLVIII by first hydrolysis of the ester using an inorganic base such as NaOH in a solvent such as $MeOH/H_2O$. Then the corresponding acid is treated with methyl lithium in an ethereal solvent such as diethyl ether affording the ketone derivative XLVIII. This ketone is then subsequently converted to the naphthol XLIX using the same chemistry as described in Scheme XI.

Scheme XIII

The preparation of naphthol intermediates LIII and LIV may be prepared using the same approach as described in Scheme IX. The bromo derivative XXXVI is converted to the alcohol L by treatment with a base such as n-butyl lithium in an organic solvent such as hexane followed by the addition of formaldehyde. The Diels-Alder reaction is acheived by heating the alcohol L in the presence of a Michael acceptor of type $Ar^2CH=CH-E$ (wherein $E=CN$, $CO_2R^{13}$, $CON(R^{12})_2$, $NO_2$, $S(O)_2R^{14}$, $S(O)_2N(R^{12})_2$, or $COR^{13}$) such as transmethylcinnamate in an organic solvent such as toluene providing the corresponding ester LI and LII. The debenzylation process to provide the naphthol intermediates LIII and LIV is described in Scheme II.

Scheme XIV

The naphthalene intermediate LV may be prepared by using naphthol such as LIII and using the same protocol described in Scheme X. The naphthol intermediate LVII may be obtained from LIII using the same protocol as described in Scheme XII.

Scheme XV

The naphthalene intermediate LVIII may be obtained by using naphthol such as LIV and using the same protocol as described in Scheme X. The naphthol intermediate LX may be prepared from LIV using the protocol described in Scheme XII.

Scheme XVI

The preparation of compounds of Formula I (wherein $X^3=-OCH_2-$) is described in Scheme XVI. The naphthalene LXI is condensed with a phenol XXXV in the presence of a phosphine such as $Ph_3P$ and an azodicarboxylate diester, in a solvent such as THF to afford Formula I compounds (wherein $X^3=-OCH_2-$).

---

SCHEME I

PREPARATION OF NAPHTHOL INTERMEDIATES (METHOD A)

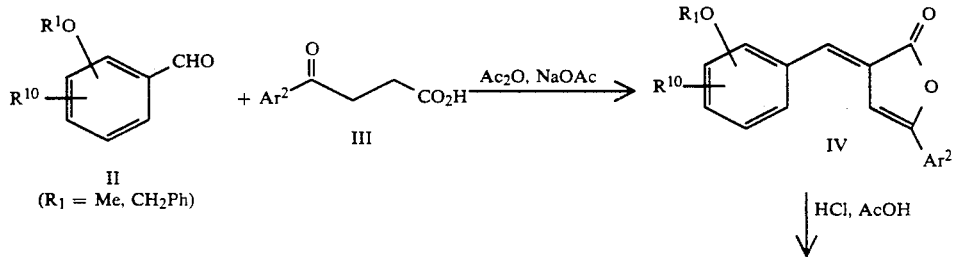

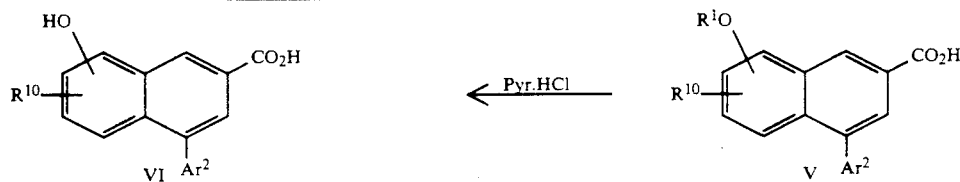
SCHEME II
PREPARATION OF NAPHTHOL INTERMEDIATES (METHOD B)
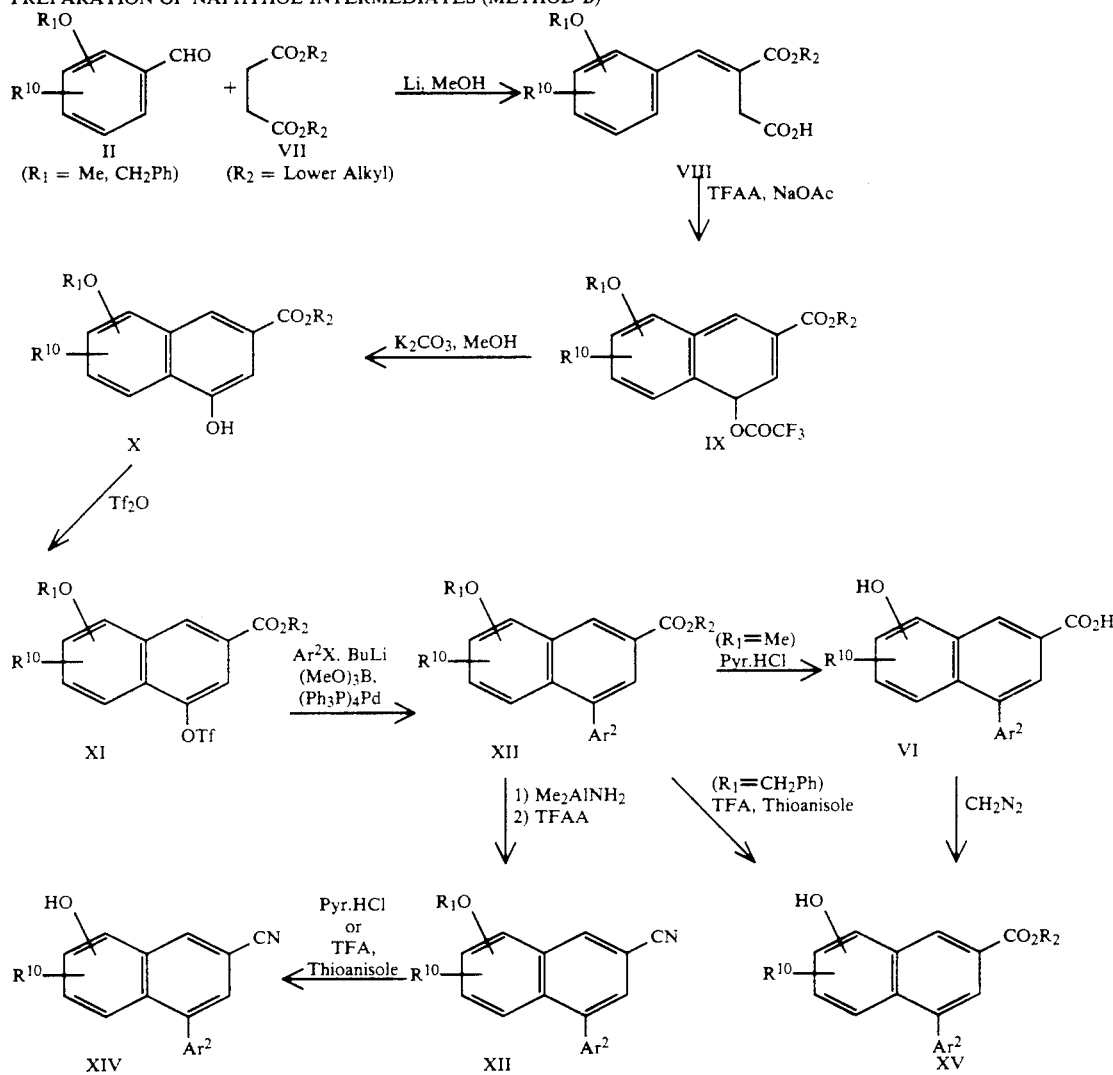
SCHEME III
PREPARATION OF NAPHTHOL INTERMEDIATES (METHOD C)
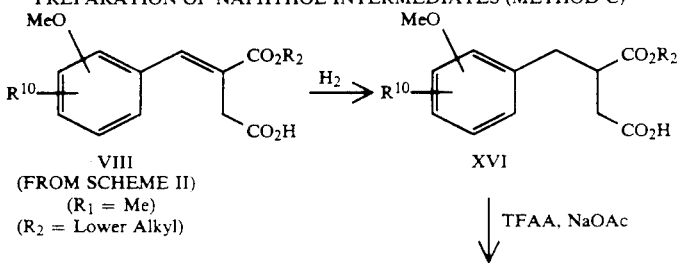

SCHEME III
PREPARATION OF NAPHTHOL INTERMEDIATES (METHOD C)

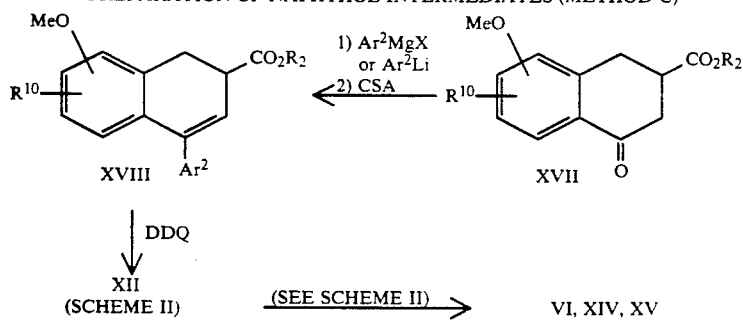

SCHEME IV
PREPARATION OF FURTHER NAPHTHOL INTERMEDIATES

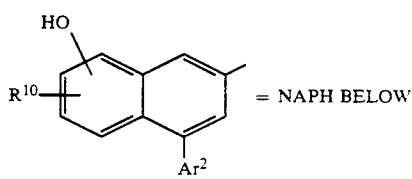 = NAPH BELOW

NAPH—H ⟵ NAPH—CO$_2$H ⟶ NAPH—COR$_2$ ⟶ NAPH—CH$_2$R$_2$
XIX     VI            XX            XXI
       (FROM SCHEME I)    (R$_2$ = Lower Alkyl)

NAPH—CO$_2$R$_2$ ⟶ NAPH—CON(R$^{13}$)$_2$    NAPH—CH$_2$OH
XXII           XXIII              XXV
(R$_2$ = Lower Alkyl)

NAPH—CN ⟶ NAPH—CHO    NAPH—CH$_2$X ⟶ NAPH—CH$_2$SR$^{14}$
XIV        XXIV           XXVI           XXVII

SCHEME V
PREPARATION OF FINAL PRODUCTS

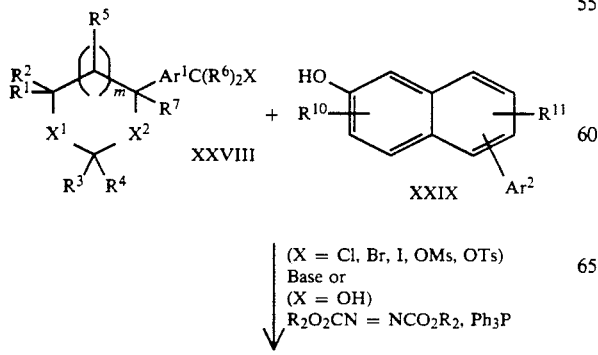

(X = Cl, Br, I, OMs, OTs)
Base or
(X = OH)
R$_2$O$_2$CN = NCO$_2$R$_2$, Ph$_3$P

-continued
SCHEME V
PREPARATION OF FINAL PRODUCTS

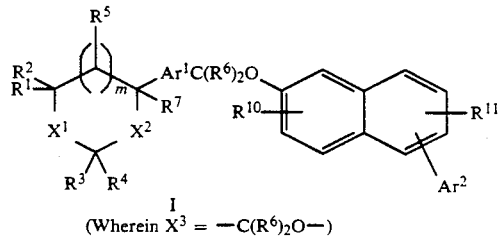

I
(Wherein X$^3$ = —C(R$^6$)$_2$O—)

SCHEME VI
PREPARATION OF FINAL PRODUCTS
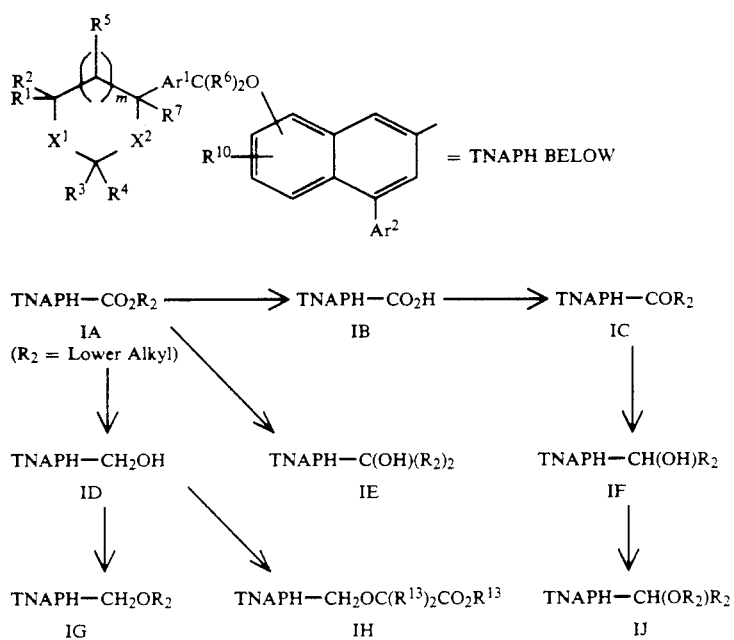
SCHEME VII
PREPARATION OF FINAL PRODUCTS
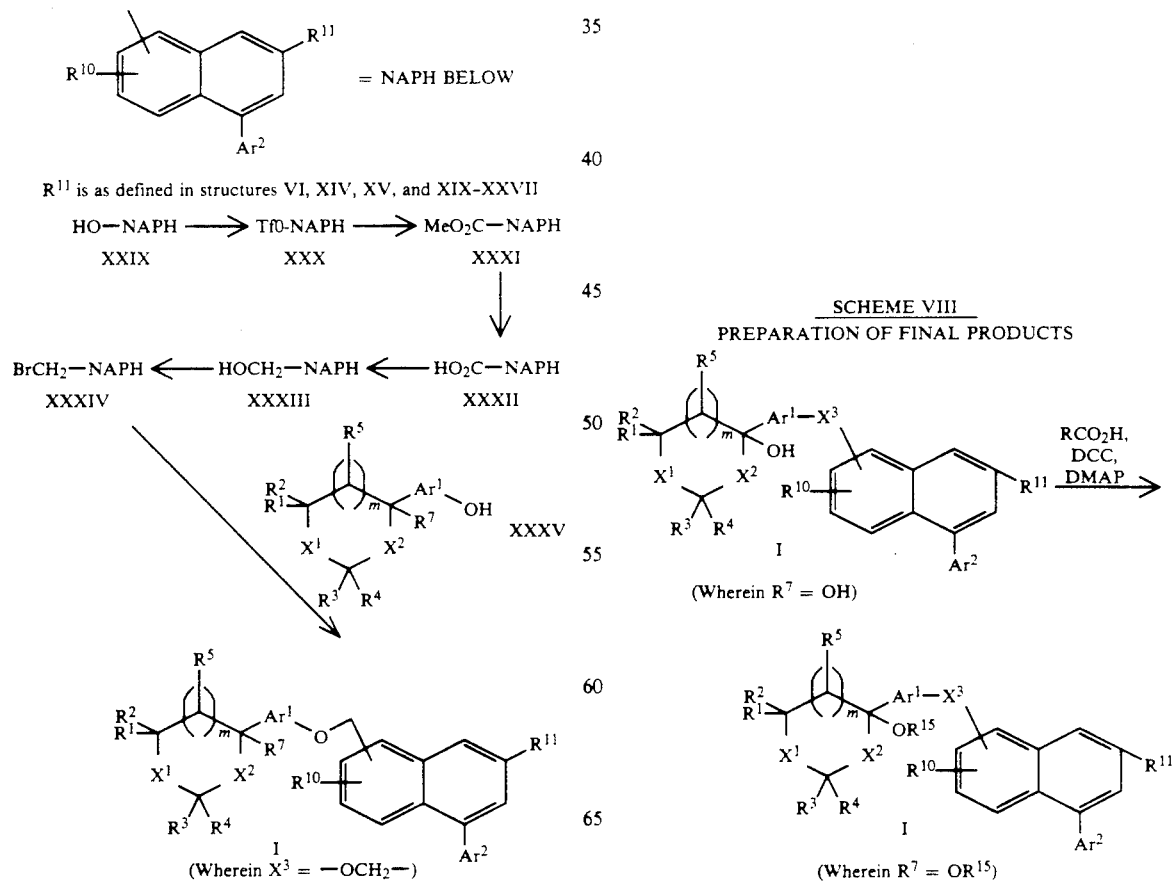
SCHEME VIII
PREPARATION OF FINAL PRODUCTS

SCHEME IX
PREPARATION OF NAPHTHOL INTERMEDIATES (METHOD D)
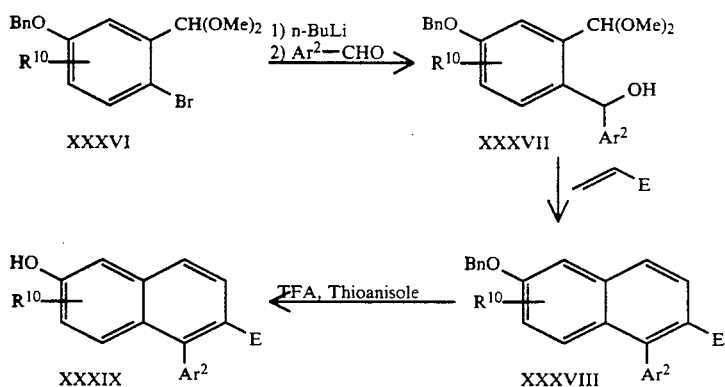
SCHEME X
FURTHER PREPARATION OF NAPHTHALENE INTERMEDIATES
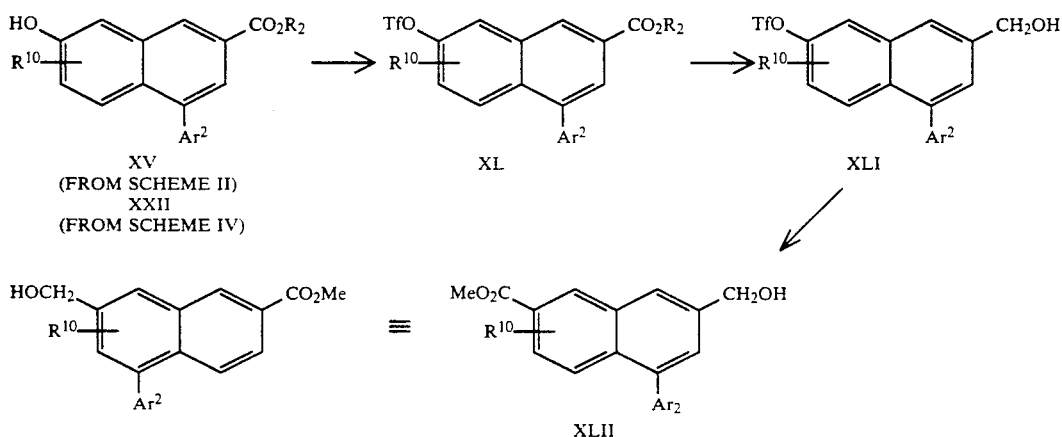
SCHEME XI
FURTHER PREPARATION OF NAPHTHOL INTERMEDIATES
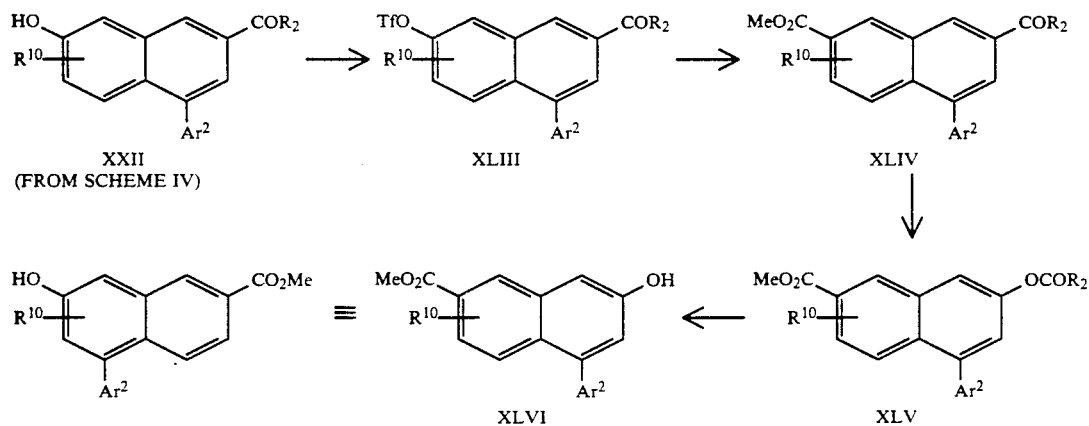

SCHEME XII
FURTHER PREPARATION OF NAPHTHALENE INTERMEDIATES
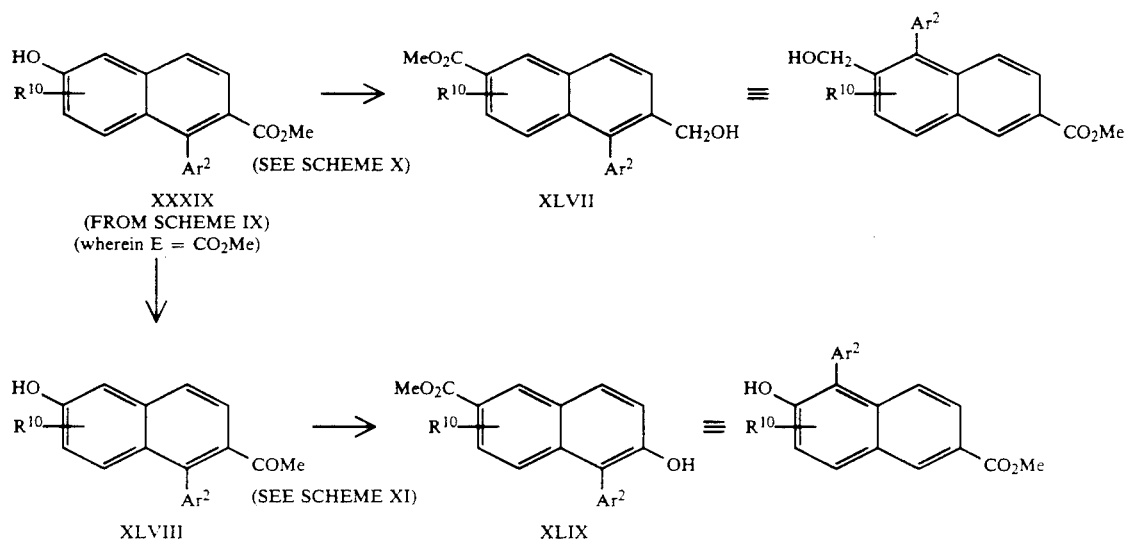
SCHEME XIII
PREPARATION OF NAPHTHOL INTERMEDIATES (METHOD E)
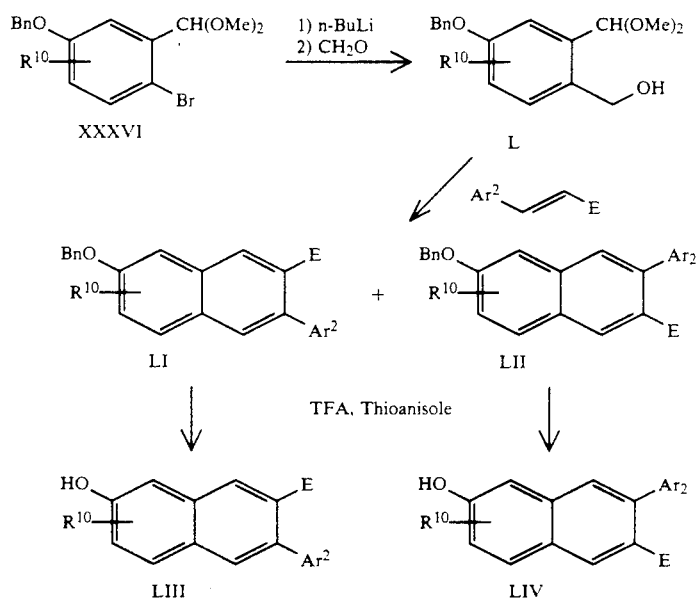
SCHEME XIV
FURTHER PREPARATION OF NAPHTHALENE INTERMEDIATES
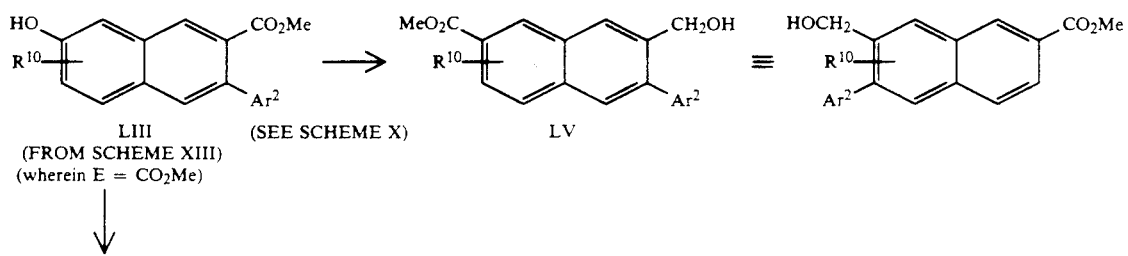

SCHEME XIV
FURTHER PREPARATION OF NAPHTHALENE INTERMEDIATES

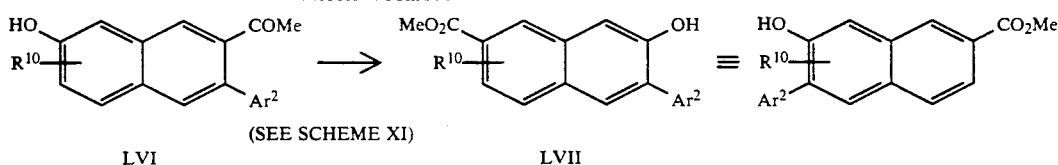

SCHEME XV
FURTHER PREPARATION OF NAPHTHALENE INTERMEDIATES

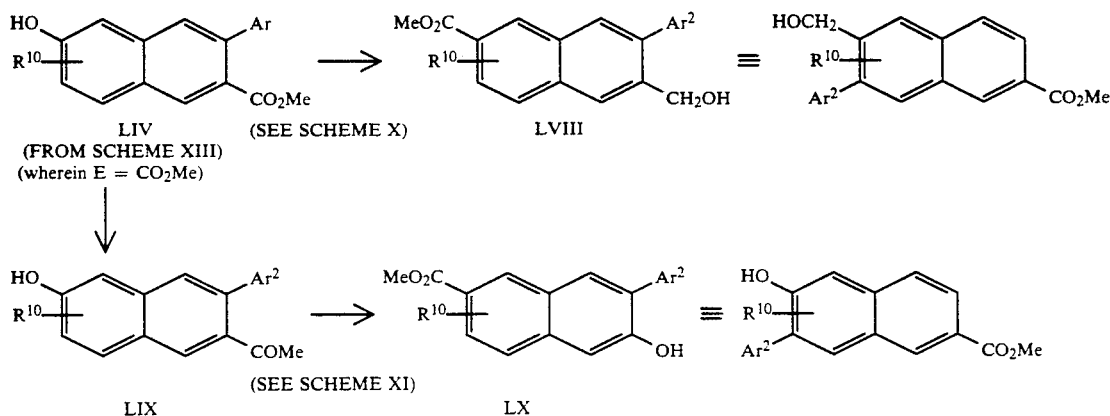

SCHEME XVI
PREPARATION OF FINAL PRODUCTS

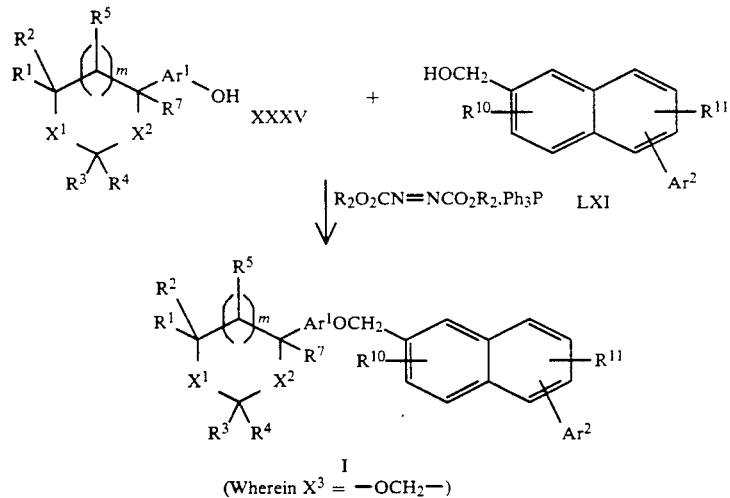

(Wherein $X^3 = -OCH_2-$)

Representative Compounds

Table I illustrates compounds of Formula Ib which are representative of the present invention.

TABLE I

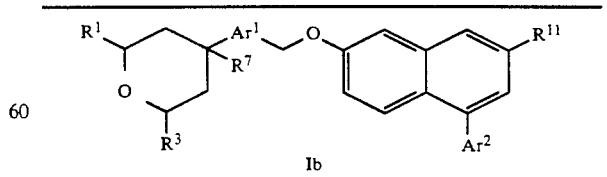

Ib

| EX. | $R^1$ | $R^3$ | $R^7$ | $Ar^1$ | $Ar^2$ | $R^{11}$ |
|---|---|---|---|---|---|---|
| 1 | H | H | OH | Phe | Ph | $CO_2Me$ |
| 2 | H | H | OH | Phe | Ph | $CO_2H$ |
| 3 | H | H | OH | Phe | Ph | COMe |
| 4 | H | H | OH | Phe | Ph | $C(OH)Me_2$ |
| 5 | H | H | OH | Phe | Ph | $CH_2OH$ |

TABLE I-continued

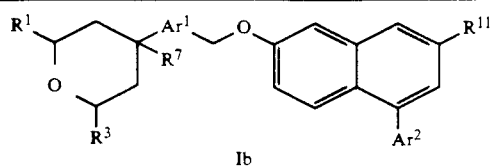

Ib

| EX. | R¹ | R³ | R⁷ | Ar¹ | Ar² | R¹¹ |
|---|---|---|---|---|---|---|
| 6 | H | H | OH | Phe | Ph | CH₂OMe |
| 7 | H | H | OH | Phe | Ph | CH(OH)Me |
| 8 | H | H | OH | Phe | Ph | CH(OMe)Me |
| 9 | H | H | OH | Phe | Ph | Et |
| 10 | H | H | OH | Phe | Ph | COBu |
| 11 | H | H | OH | Phe | Ph | CONMe₂ |
| 12 | H | H | OH | Phe | Ph | CH₂SPh |
| 13 | H | H | OH | Phe | Ph | CH₂SMe |
| 14 | H | H | OH | Phe | Ph | CH₂CN |
| 15 | H | H | OH | Phe | Ph | COCH₂SMe |
| 16 | H | H | OH | Phe | Ph | CH₂OCH₂CO₂Me |
| 17 | H | H | OH | Phe | Ph | CN |
| 18 | H | H | OH | Phe | 3-Fu | CN |
| 19 | H | H | OH | Phe | 3-Fu | CO₂Me |
| 20 | H | H | OH | Phe | 3-Fu | CHO |
| 21 | H | H | OH | 5,3-Pye | 3-Fu | CN |
| 22 | —CH₂O— | | OH | 5,3-Pye | 3-Fu | CN |
| 23 | —CH₂O— | | OH | Phe | 3-Fu | CN |
| 24 | H | H | OH | 2,4-Tze | 3-Fu | CN |
| 25* | Me | H | OH | Phe | 3-Fu | CN |
| 26** | Me | H | OH | Phe | 2-Fu | CN |
| 27** | Me | H | OMe | Phe | 3-Fu | CN |
| 28 | —CH₂O— | | OMe | Phe | 3-Fu | CN |
| 29 | H | H | OH | 6,2-Pye | 3-Fu | CN |
| 30* | Me | Me | OH | Phe | 3-Fu | CN |
| 31 | —CH₂O— | | OH | Phe | 2-Th | CN |
| 32 | —CH₂O— | | OH | Phe | 3-Th | CN |
| 33 | —CH₂O— | | OMe | Phe | 3-Th | CN |
| 34 | H | H | OH | 5,3-Pye | 3-Th | CN |
| 35 | H | H | OH | Phe | 3-Th | CN |
| 36 | —CH₂O— | | OH | 5,3-Pye | 3-Th | CN |
| 37 | H | H | OH | Phe | 2-Tz | CO₂Me |
| 38 | H | H | OH | Phe | 5-Tz | CO₂Me |
| 39 | H | H | OH | Phe | Ph | H |
| 40 | H | H | OH | 4,2-Pye | 3-Fu | CN |
| 41 | H | H | OMe | 6,2-Pye | 3-Fu | CN |
| 42 | —CH₂O— | | OH | 6,2-Pye | 3-Fu | CN |
| 43 | —CH₂O— | | OMe | 6,2-Pye | 3-Fu | CN |
| 44 | —CH₂O— | | OH | 4,2-Pye | 3-Fu | CN |
| 45 | —CH₂O— | | OMe | 4,2-Pye | 3-Fu | CN |
| 46 | —CH₂O— | | OH | 2,4-Pye | 3-Fu | CN |
| 47 | —CH₂O— | | OMe | 2,4-Pye | 3-Fu | CN |

TABLE I-continued

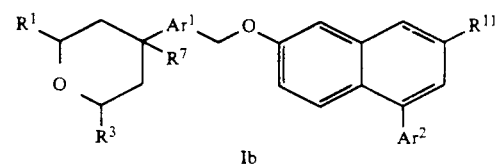

Ib

| EX. | R¹ | R³ | R⁷ | Ar¹ | Ar² | R¹¹ |
|---|---|---|---|---|---|---|
| 48 | H | H | OH | 2,4-Pye | 3-Fu | CN |
| 49 | H | H | OMe | 2,4-Pye | 3 Fu | CN |
| 50 | H | H | OH | 6,2-Pye | 3-Th | CN |
| 51 | H | H | OH | 2,4-Pye | 3-Th | CN |
| 55 | CH₂OH | OH | OH | 6,2-Pye | 3-Fu | CN |
| 56 | —CH₂O— | | OH | 6,2-Pye | 3-Th | CN |
| 57 | H | H | OH | Phe | 5-Pym | CO₂Me |
| 58 | —CH₂O— | | OH | 6,2-Pye | 3-Fu | COMe |
| 59 | H | H | OH | Phe | 3-Fu | CH₂N(OH)COMe |
| 60 | H | H | OH | Phe | Tet | CO₂Me |
| 61 | H | H | OH | Phe | 2-MeTet | CO₂Me |
| 72 | —CH₂O— | | OH | 6,2-Pye | 3-Fu | CN |

*α isomer
**β isomer

Table II illustrates compounds of Formula Ic which are further representatives of the present invention.

TABLE II

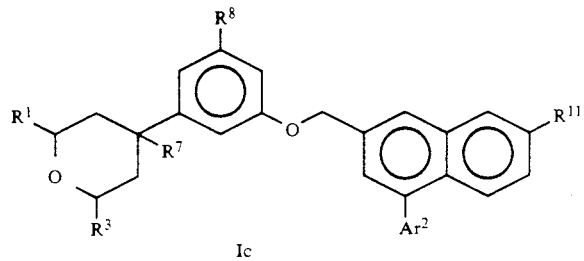

Ic

| EX. | R¹ | R³ | R⁷ | R⁸ | Ar² | R¹¹ |
|---|---|---|---|---|---|---|
| 54 | —CH₂O— | | OH | F | Ph | CO₂Me |
| 62 | —CH₂O— | | OH | F | Ph | CN |
| 63 | —CH₂O— | | OH | F | 3-Fu | CO₂Me |
| 64 | —CH₂O— | | OH | F | 3-Fu | CN |
| 65 | —CH₂O— | | OMe | F | 3-Fu | CN |
| 66 | —CH₂O— | | OMe | H | 3-Fu | CN |
| 67 | —CH₂O— | | OMe | F | 3-Th | CN |
| 68 | H | H | OMe | F | 3-Fu | CN |
| 69 | H | H | OMe | F | 3-Th | CN |
| 70 | H | H | OMe | F | Ph | CO₂Me |
| 71 | H | H | OMe | F | Ph | CN |

Table III illustrates compounds of Formula Id which are further representatives of the present invention.

TABLE III

Id

| R¹⁵ | Ar² | R¹¹ |
|---|---|---|
| —CO(CH₂)₂CO₂H | Ph | COCH₃ |
| —CO(CH₂)₂CO₂H | Ph | CN |
| —CO-3-Py | Ph | CN |
| —CO(CH₂)₂CO₂Me | Ph | CN |
| —COCH₂NH₂ | Ph | CN |
| —COCH₂OH | 3-Fu | CN |
| —COCH₂NH₂ | 3-Fu | CN |

TABLE III-continued

Id

[Chemical structure showing a benzene ring connected via CH2-O linker to a naphthalene ring bearing R11 and Ar2 substituents, with an OR15 group and an oxygen-containing ring]

| R15 | Ar2 | R11 |
|---|---|---|
| —COCH$_2$NMe$_2$ | 3-Fu | CN |
| —COCH$_2$NMe$_2$ | Ph | CN |
| —COCH$_2$NHMe | 3-Fu | CN |
| —COCH(NH$_2$)CH$_2$CO$_2$Me | 3-Fu | CN |
| —COCH(NHt-BOC)CH$_2$CO$_2$H | 3-Fu | CN |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000x g supernatant fraction prepared from insect cells infected with recombinant baculovirus containing the coding sequence for human 5-lipoxygenase. Enzyme activity is measured spectrophotometrically from the optimal rate of conjugated diene formation (A$_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000x g fraction from S19 cells infected with the recombinant baculovirus rvH5LO (8-1) containing the coding region sequence for human 5-lipoxygenase is prepared as described by Denis et al. (J. Biol. Chem., 266, 5072–5079 (1991)). The enzymatic activity is measured, using a spectrophotometric assay from the optimal rate of conjugated diene formation (A$_{234}$) using the procedure described by Riendeau et al. (Biochem. Pharmacol., 38, 2323-2321, 1989) with minor modifications. The incubation mixture contains 50 mM sodium phosphate pH 7.4, 0.2 mM ATP, 0.2 mM CaCl$_2$, 20 μM arachidonic acid (5 μL from a 100-fold concentrated solution in ethanol), 12 μg/mL phosphatidylcholine, an aliquot of the 100,000x g fraction (2–10 μL) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length and 4 mm internal width). The absorbance changes are recorded with a Hewlett-Packard diode array spectrophotometer (HP 8452A) connected to the ChemStation using UV/VIS Kinetics Software (Hewlett-Packard). Enzymatic activity is calculated from the optimal rate of the reaction by a linear fit of the variation of A$_{234}$ during the first twenty seconds using the least square method for the equation A$_{234}$=V$_o$t+A$_o$ where V$_o$ is the rate, t is the time and A$_o$ is the absorbance at zero time. The results are expressed as percentages of inhibition of the reaction rate relative to controls containing the DMSO vehicle.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15–24 hr. the rats are sacrificed (CO$_2$) and the cells from the peritoneal cavity are recovered by lavage with 20 mL of buffer (Eagles MEM containing 30 mM HEPES adjusted to pH 7.4 with NaOH). The cells are pelleted (350× g, 5 min.), resuspended in buffer with vigorous shaking, filtered through lens paper, recentrifuged and finally suspended in buffer at a concentration of 10 cells/mL. A 500 μL aliquot of PMN suspension and test compound are preincubated for 2 minutes at 37° C., followed by the addition of 10 μM A-23187. The suspension is stirred for an additional 4 minutes then bioassayed for LTB$_4$ content by adding an aliquot to a second 500 μL portion of the PMN at 37° C. The LTB$_4$ produced in the first incubation causes aggregation of the second PMN, which is measured as a change in light transmission. The size of the assay aliquot is chosen to give a submaximal transmission change (usually −70%) for the untreated control. The percentage inhibition of LTB$_4$ formation is calculated &rom the ratio of transmission change in the sample to the transmission change in the compound-free control.

Human Polymorphonuclear (PMN) Leukocyte LTB$_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypague (specific gravity 1.077), as described by Boyum, A., Scand. J. Clin. Lab. Invest., 21 (Supp 97), 77, (1968). Contaminating erythrocytes are removed by lysis following exposure to ammonium chloride (0.16M) in Tris buffer (pH 7.65), and the PMNs resuspended at 5×10$^5$ cells/mL in HEPES (15 mM)-buffered Hanks balanced salt solution containing Ca$^{2+}$ (1.4 mM) and Mg$^{2+}$ (0.7 ). pH 7.4. Viability is assessed by Trypan blue exclusion.

B. Generation and Radioimmunoassay of LTB$_4$. PMNs (0.5 mL; 2.5×10$^5$ cells) are placed in plastic tubes and incubated (37° C., 2 min) with test compounds at the desired concentration or vehicle (DMSO, final concentration 0.2%) as control. The synthesis of LTB$_4$ is initiated by the addition of calcium ionophore A23187 (final concentration 10 μM) or vehicle in control samples and allowed to proceed for 5 minutes at 37° C. The reactions are then terminated by the addition of cold methanol (0.25 mL) and samples of the entire PMN reaction mixture are removed for radioimmunoassay of LTB$_4$.

Samples (50 μL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-LTB$_4$ (10 nCi in 100 μL RIA buffer) and LTB$_4$-antiserum (100 μL of a 1:3000 dilution in RIA buffer) are added and the tubes vortexed. Reactants are allowed to equilibrate by incubation overnight at 4° C. To separate antibody-bound from free $LTB_4$, aliquots (50 μL) of activated charcoal (3% activated charcoal in RIA buffer containing 0.25% Dextran T-70) are added, the tubes vortexed, and allowed to stand at room temperature for 10 minutes prior to centrifugation (1500×g; 10 min; 4° C. The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al. Prostaglandins Leukotrienes and Medicine, 13, 21 (1984). The amount of $LTB_4$ produced in test and control samples is calculated. Inhibitory dose-response curves are constructed using a four-parameter algorithm and from these the $IC_{50}$ values determined.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigens, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 6 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a Devilbiss ultrasonic nebulizer is utilized. Pretreatment periods vary from 5 minutes to 4 hours before the monkeys are challenged with aerosol doses of Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of Ascaris antigen response by the test compound. For statistical analysis, paired t-test is used. (See McFarlane, C .S. et al., Prostaglandins, 28:173–182, 1984, and McFarlane, C. S. et al., Agents Actions 22:63–68, 1987.)

Prevention of Induced Bronchonconstriction in Allergic Sheep

A. Rationale. Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The affects of antigen in these sheep are largely observed in the large airways and are conveniently monitored as changes in lung resistance or specific lung resistance.

B. Methods. Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (Abraham, W. M. et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). Testing of the pressure transcuder catheter system reveals no phase shift between pressure and flow to a frequency of 9 Hz. For the measurement of pulmonary resistance ($R_l$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_l$ from transpulmonary pressure, respiratory volume obtained by integration and flow. Analysis of 10–15 breaths is used for the determination of $R_l$. Thoracic gas volume ($V_{tg}$) is measured in a body plethysmograph, to obtain specific pulmonary resistance ($SR_l = R_l.V_{tg}$).

Aerosol Delivery Systems: Aerosols of *Ascaris suum* extract (1:20) are generated using a disposable medical-nebulizer (Raindrop®, Puritan Bennett), which produces an aerosol with a mass median aerodynamic diameter of a 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with Ascaris suum antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to ascaris challenge and for 8 hrs after ascaris as described above.

Statistical Analysis: A Kruskal-Wallis one way ANOVA test is used to compare the acute immediate responses to antigen and the peak late response in the controls and the drug treated animals.

PREPARATION OF BENZYL HALIDES

Halide 1: 3-[4-(4-methoxy)tetrahydropyranyl]benzyl bromide

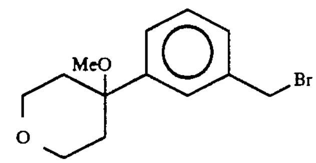

Step 1: 3-[4-(4-hydroxy)tetrahydropyranyl]toluene

To a solution of 3-bromotoluene (24.3 mL; Aldrich) in THF (250 mL) stirred at −78° C. was added a solution of n-BuLi in hexane (1.75M; 114 mL; Aldrich). After 45 min., the resulting white suspension was treated with a solution of tetrahydropyran-4-one (18.5 mL; Aldrich) in THF (125 mL). After 45 min. at −78° C., the mixture was stirred for 1.5 hr. at r.t. Saturated aqueous $NH_4Cl$ was then added and the organic phase separated. The aqueous phase was extracted with EtOAc. The combined organic phases were washed with brine, dried ($MgSO_4$) and evaporated. Flash chromatography of the residue (silica gel; hexane/EtOAc (1:1) followed by crystallization in hexane/EtOAc afforded the title compound as a white solid.

Step 2: 3-[4-(4-Methoxy)tetrahydropyranyl]toluene

To a 0° C. solution of the alcohol from Step 1 (38 g) in DMF (300 mL) were added NaH (60% in mineral oil; 16 g) and methyl iodide (31 mL). The mixture was stirred under nitrogen at r.t. for 15 hr. before $H_2O$ (1 L) was added. The aqueous phase was extracted with EtOAc and the combined organic phases were washed with brine, dried ($MgSO_4$) and evaporated. Flash chromatography of the residue (silica gel; hexane/EtOAc (4:1) yielded the title ether as a colorless liquid.

Step 3: 3-[4-(4-Methoxy)tetrahydropyranyl]benzylbromide

A mixture of the toluene (16 g) from Step 2, N-bromosuccinimide (14.6 g) and azoisobutyronitrile (AIBN) (127 mg) in $CCl_4$ (250 mL) was refluxed for 1.5 hr. Filtration and evaporation of the filtrate gave the desired benzyl bromide.

Halide 2: 3-[4-(4-Hydroxy)tetrahydropyranyl]benzylbromide

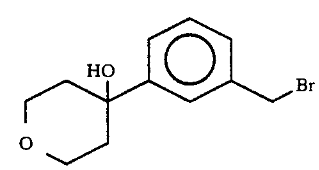

Following the procedure described for Halide 1, Step 3, but substituting 3-[4-(4-hydroxy)tetrahydropyranyl]-toluene (from Halide 1, Step 1) for 3-[4-(4-methoxy)tetrahydropyranyl]toluene, the title product was obtained as a yellow solid.

Halide 3:
3-[4-(4β-Hydroxy-2,6-dimethyl)tetrahydropyranyl]benzyl bromide

Step 1: 3-Bromo-O-tetrahydropyranylbenzyl alcohol

To a solution of 3-bromobenzyl alcohol (11.5 g; Aldrich) dissolved in CH$_2$Cl$_2$ (100 mL) at 0° C. and p-toluenesulfonic acid monohydrate (116 mg) was added DHP (6.2 mL). The resulting solution was stirred at r.t. for 3 hr. then was quenched with NH$_4$OAc. The aqueous phase was extracted with CH$_2$Cl$_2$. The combined organic phases were washed with brine, dried (MgSO$_4$) and evaporated. Flash chromatography of the residue (silica gel: hexane/EtOAc (9:1) afforded the title compound as an oil.

Step 2: 2,6-Dimethyltetrahydropyran-4-one

A solution of 2,6-dimethyl-γ-pyrone (17 g, Aldrich) in 300 mL of EtOH 95% was hydrogenated for 3 days under 70 psi. After filtration over celite, the solvent was evaporated and replaced by CH$_2$Cl$_2$. The solution was then treated with celite (30 g) and PCC (48.5 g). The suspension was stirred for 3 hr. and the reaction was diluted with Et$_2$O (300 mL) and then filtered over a pad celite. The filtrate was evaporated to dryness and the residual solution was then chromatographed using hexane/Et$_2$O (1:1) to give the title compound.

Step 3: 3-[4-(4β-Hydroxy-2,6-dimethyl)tetrahydropyranyl]-O-tetrahydropyranylbenzyl alcohol Following the procedure described in Halide 1, Step 1, but substituting 3-bromo-O-tetrahydropyranylbenzyl alcohol (from Step 1) for 3-bromotoluene and substituting 2,6-dimethyltetrahydropyran-4-one (from Step 2) for tetrahydropyran-4-one, the title compound was obtained as a mixture of α and β isomers (30:70). Both isomers were isolated from a flash column (hexane/EtOAc) (6:4). The β-hydroxy isomer is more polar than the α-hydroxy isomer.

Step 4: 3-[4β-Hydroxy-2,6-dimethyl)tetrahydropyranyl]benzyl alcohol

The β-hydroxy-THP derivative (1.0 g) from Step 3, was dissolved in EtOH (10 mL) and treated with of p-toluenesulfonic acid (30 mg). The reaction was stirred at r.t. for 90 min. The EtOH was evaporated and the resulting syrup was flash chromatographed to give the title compound.

Step 5: 3-[4-(4β-Hydroxy-2,6-dimethyl)tetrahydropyranyl]benzyl bromide

To a solution of the alcohol (183 mg) from Step 4 in CH$_2$Cl$_2$ (9 ml) was added CBr$_4$ (269 mg). The reaction was then cooled at −30° C. and DIPHOS (298 mg) was added in portions. After 10 min., the reaction was quenched with a solution (10 mL) of 10% EtOAc in hexane and without evaporation, the solvent was poured onto a silica gel column and eluted with EtOAc/hexane (3:7) affording the title compound.

Halide 4:
3-[4-(4αHydroxy-2,6-dimethyl)tetrahydropyranyl]benzyl bromide

Following the procedure described in Halide 3, Step 4–5, but substituting α-hydroxy-THP derivative (from Halide 3, Step 3) for β-hydroxy-THP derivative, the title product was obtained.

Halide 5:
4-Bromomethyl-2-[4-(4-hydroxy)tetrahydropyranyl]thiazole

Step 1: 4-Methyl-2-[4-(4-hydroxy)tetrahydropyranyl]thiazole

To a solution of 4-methyl thiazole (990 mg) in THF (10 mL) at −78° C. there was added n-BuLi (1.1M) in hexanes (10 mL). The resulting suspension was stirred at −78° C. for 45 min. then there was added slowly a solution of tetrahydro-4H-pyran-4-one (1.20 g) in THF (2 mL). The mixture was then stirred at 0° C. for 1 hr., then quenched with saturated aqueous NH$_4$Cl (8 mL), and diluted with EtOAc. The organic phase was washed (3×) with brine, dried and evaporated to a residue which was chromatographed on silica gel, eluting with a 1:1 mixture of EtOAc and hexane to afford the product as a light yellow solid.

Step 2: 4-Bromomethyl-2-[4-(4-hydroxy)tetrahydropyranyl]thiazole

Following the procedure described in Halide 1, Step 3, but substituting 4-methyl-2-[4-(4-hydroxy)tetrahydropyranyl]thiazole from Step 1, for 3-[4-(4-methoxy)-tetrahydropyran]toluene, the title product was obtained as a white solid.

Halide 6:
3-[4-(2,2-Dimethyl-4-ethyl-1,3-dioxalanyl)]benzyl bromide

Step 1: 3-Methylpropiophenone

To a 0° C. solution of EtMgBr in Et$_2$O (3.0M, 570 mL, Aldrich) was slowly added m-tolunitrile (102 mL, Aldrich). After stirring at r.t. for 19 hr., benzene (300 mL) was added and the resulting mixture was cooled to 0° C. HCl (6N, 600 mL) was then slowly added. The organic phase was separated, washed with 5% NaHCO$_3$ and brine, dried (MgSO$_4$) and evaporated to afford the desired ketone as a yellow liquid.

Step 2: 3-[2-(1-Isopropoxydimethylsilylbutan-2-ol)]toluene

A solution of the ketone from Step 1 (2.5 g) in THF (15 mL) was added dropwise to a 0° C. solution of isopropoxydimethylsilylmethylmagnesium chloride (5.6 mmoL, J. Org. Chem., 1983, 48, 2120) in THF (10 mL). The mixture was stirred at r.t. under argon for 2 hr. before it was washed with saturated NH4Cl solution and brine, dried (MgSO4) and evaporated. Flash chromatography of the residue (silica gel; hexane/EtOAc (95:5)) yielded the title alcohol as a colorless oil.

Step 3: 3-[2-(Butane-1,2-diol)]toluene

A mixture of the alcohol from Step 2 (3.67 g), THF (20 mL), MeOH (20 mL), NaHCO3 (1.25 g) and H2O2 (30%) (12.8 mL) was refluxed for 3 hr. After evaporation, the residue was taken up in EtOAc and the organic phase was washed with brine, dried (MgSO4) and evaporated. Flash chromatography of the residue (silica gel; hexane/EtOAc (3:2)) yielded the desired diol as a colorless oil.

Step 4: 3-[4-(2,2-Dimethyl-4-ethyl-1,3-dioxalanyl)-]toluene

Concentrated sulphuric acid (1 drop) was added to a solution of the diol from Step 3 (1.0 g) in acetone (50 mL). The reaction mixture was stirred for 2 hr. at r.t. before it was neutralized by the addition of 1N NaOH and evaporated. Flash chromatography of the residue (silica gel; hexane/EtOAc (75:5)) afforded the title toluene as a colorless oil.

Step 5: 3-[4-(2,2-Dimethyl-4-ethyl-1,3-dioxalanyl)]-benzyl bromide

Following the procedure described in Halide 1, Step 3, but substituting the toluene from Step 4, for 3-[4-(4-methoxy)tetrahydropyranyl]toluene, the title benzyl bromide was obtained as an oil.

PREPARATION OF ALCOHOLS

Alcohol 1: 3-[4-(4-Hydroxy)tetrahydropyranyl]benzyl alcohol

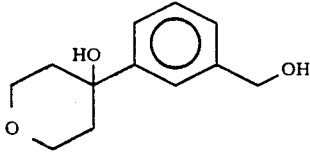

Step 1: 3-Bromo-O-tert-butyldiphenylsilylbenzylalcohol

To a solution of 3-bromobenzyl alcohol (25 g, 134 mmoL) in anhydrous DMF (300 mL) was added triethylamine (17.6 g, 174 mmoL) followed by t-butyldiphenylsilyl chloride (40.4 g, 147 mmoL). The mixture was stirred for 24 hr, poured into a saturated aqueous NH4Cl solution (1 L), and extracted with Et2O. The combined organic layers were washed with brine, dried over MgSO4 and evaporated. Flash chromatography on silica gel (2.5% EtOAc in hexane) afforded the title compound as a colorless oil.

Step 2: 3-[4-(4-Hydroxy)tetrahydropyranyl]benzylalcohol

Following the procedure described in Halide 1, Step 1, but substituting 3-bromo-O-tert-butyldiphenylsilylbenzyl alcohol (from Step 1) for 3-bromotoluene, the tert-butyldiphenylsilylether derivative of the title compound was obtained. The crude product was treated with 5 equivalents of Bu4NF in dry THF at r.t. for 1.5 hr. After evaporation of the solvent, the crude product was flash chromatographed on silica gel (toluene:EtOAc/1:4) to afford the pure title compound as a colorless oil.

Alcohols 2 and 3:
3-[4-(4α-Hydroxy-2-methyl)tetrahydropyranyl]benzyl alcohol (2) and
3-[4-(4β-hydroxy-2-methyl)tetrahydropyranyl]benzyl alcohol (3)

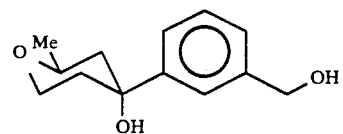

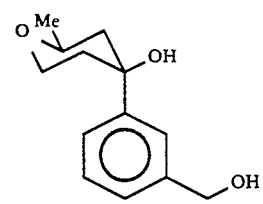

Following the procedure in Halide 1, Step 1, but substituting 3-bromo-O-tert-butyldiphenylsilylbenzyl alcohol (from Alcohol 1, Step 1) for 3-bromotoluene and substituting 2-methyltetrahydropyran-4-one (JACS, 1982, 104, 4666) for tetrahydropyran-4-one. The tert-butyldiphenylsilylether derivatives of the title compounds were obtained as a mixture of α and β-isomers. This mixture was then treated with 5 equivalents of Bu4NF in dry THF at r.t. for 1.5 hr. After evaporation of the solvent both isomers were separated by using flash chromatography (toluene:EtOAc/1:4) affording first the α-hydroxy isomer (Alcohol 2) followed by the β-isomer (Alcohol 3) in a ratio 1:2.8.

Alcohol 4: [1S,5R]
3-[3-(3α-Hydroxy-6,8-dioxabicyclo[3.2.1]octanyl)]benzyl alcohol

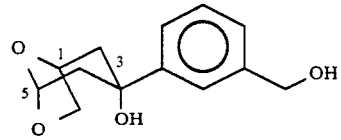

Step 1: 2,4-Di-O-p-toluenesulfonyl-1,6-anhydro-β-D-glucose

To a solution of 1,6-anhydro-β-D-glucose (50 g, 308 mmoL) in dry pyridine (100 mL) at 0° C. was added dropwise to a solution of p-toluenesulfonyl chloride (123 g, 647 mmoL) dissolved in CHCl3 (350 mL) and pyridine (200 mL). The reaction mixture was stirred at r.t. for at least 2 days. Water was added and the reaction mixture was stirred for 1 hr, then the organic layer was decanted and the aqueous phase was reextracted with CHCl3. The combined organic layers were washed with H2SO4 (10%) until the pH remained acidic, then finally washed with a saturated NH4OAc solution. The resulting organic layer was dried over MgSO4 and the solvent evaporated. The syrup obtained was flash chromatographed on silica gel eluting with hexane:EtOAc (1:1) to give the title compound an oil.

Step 2: [1S,3S,5R] 6,8-Dioxabicyclo[3.2.1]octan-3-ol

The ditosylate derivative from Step 1 (107 g, 0.228 mmoL) was dissolved in THF (1.6 L) at −40° C. and Super-hydride in THF (800 mL, 1M, 0.8 mmoL) was slowly added. The resulting reaction mixture was stirred at r.t. overnight. The reaction was cannulated into cold H$_2$O (226 mL) using external cooling, then NaOH 3N (640 mL, 1.92 mmol) and H$_2$O$_2$ (30%) (490 mL, 4.3 mmol) were successively added. The reaction was stirred at r.t. for 1 hr, then the supernatant (THF layer) was separated from the aqueous layer and concentrated. The resulting residue was combined with the aqueous layer and extracted with CH$_2$Cl$_2$ using a continuous extractor. The organic layer was dried (MgSO$_4$) and evaporated to dryness. The oily residue was dissolved in hot Et$_2$O, filtered and evaporated to dryness affording the title compound contaminated with the 2-octanol isomer. The crude product was used as such for the next step.

Step 3: [1S,5R] 6,8-dioxabicyclo[3.2.1]octan-3-one

The crude alcohol from Step 2 (16.6 g, 89 mmoL) in CH$_2$Cl$_2$ (200 mL) was added slowly to a suspension of PCC (38.4 g, 178 mmoL) and celite (22 g) in CH$_2$Cl$_2$ (400 mL) and stirred for 1 hr. The reaction mixture was diluted with Et$_2$O (600 mL) and filtered over celite. The filtrate was evaporated and the residue distilled with a Kügelrohr apparatus (100° C., 1.8 mm/Hg) affording the title product as an oil.

Step 4: [1S,5R] 3-[3-(3α-Hydroxy-6,8-dioxabicyclo[3.2.1]octanyl]benzyl alcohol Following the procedure described in Halide 1, Step 1, but substituting 3-bromo-O-tert-butyldiphenyl-silyl-benzyl alcohol (from Alcohol 1, Step 1) for 3-bromotoluene, the tert-butyldiphenyl-silylether derivative of the title compound was obtained. The crude product was treated with 1 equivalent of Bu$_4$NF in dry THF at r.t. for 1.5 hr. After evaporation of the solvent, the crude product was flash chromatographed on silica gel (hexane:EtOAc, 4:1) to afford the pure title product as a colorless oil.

Alcohol 5:
5-[4-(4-Hydroxy)tetrahydropyranyl]pyridin-3-ylmethanol

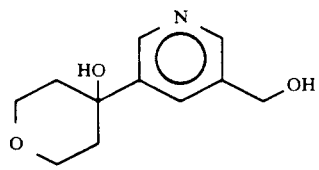

Step 1: 5-Bromo-O-tert-butyldiphenylsilylpyridin-3-ylmethanol

To a solution of 5-bromopyridin-3-ylmethanol (Chem. Pharm. Bull. 1990, 38, 2446) (29 g, 154 mmoL) and tert-butylchlorodiphenylsilane (47.5 g, 173 mmoL) in CH$_2$Cl$_2$ (500 mL) at r.t., there was added imidazole (15.8 g, 232 mmoL). The mixture was stirred for 1 hr. and filtered. The filtrate was evaporated and the residue chromatographed on silica gel eluting with a 1:7 mixture of EtOAc and hexane, to afford the product as a colorless oil.

Step 2: 5-[4-(4-Hydroxy)tetrahydropyranyl]-O-tert-butyldiphenylsilylpyridin-3-ylmethanol To a solution of the silylether from Step 1 (50 g, 117 mmoL) in THF (500 mL), cooled to −70° C., there was slowly added n-BuLi 1.12M in hexanes (115 mL, 129 mmoL) affording a dark brown solution. To this, there was added a solution of tetrahydro-4H-pyran-4-one (14.1 g, 141 mmoL) in THF (925 mL). The resulting mixture was stirred for 1 hr. at −70° C., then quenched slowly with saturated aqueous NH$_4$Cl (50 mL) and allowed to warm up to r.t. After diluting with EtOAc (500 mL) the mixture was washed (4×) with brine, dried over Na$_2$SO$_4$ and evaporated. Chromatography on silica gel, eluting with EtOAc, afforded the product as an oil which solidified.

Step 3: 5-[4-(4-Hydroxy)tetrahydropyranyl]pyridin-3-ylmethanol

To a solution of the silylether from Step 2 (20.35 g, 45.5 mmoL) in THF (350 mL), there was added Bu$_4$NF 1M in THF (52 mL) and the mixture was stirred at r.t. for 1 hr. The solvent was evaporated and the residue chromatographed as a short column of silica gel, eluting with a 1:4 mixture of EtOH and EtOAc to afford the title product which was obtained, after trituration with Et$_2$O and filtration, as a light yellow solid; m.p. 145°–147° C.

Alcohol 6:
6-[4-(4-Hydroxy)tetrahydropyranyl]pyridin-2-ylmethanol

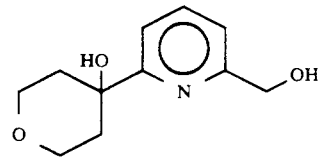

Step 1: 2-Bromo-6-[4-(4-hydroxy)tetrahydropyranyl]pyridine

A solution of 2,6-dibromopyridine (15 g) in Et$_2$O (375 mL) was cooled to −78° C. To the resulting suspension was slowly added n-BuLi 2M in hexanes (47.5 mL, 0.9 eq.) and the resulting mixture was stirred for a further 15 min. at −78° C. There was slowly added a solution of tetrahydro-4H-pyran-4-one (11.6 g) in Et$_2$O (25 mL). The resulting white suspension was stirred at −78° C. for an additional 15 min. There was added saturated aqueous NH$_4$Cl (100 mL) and the mixture was allowed to warm up to r.t. After dilution with EtOAc, the organic phase was washed (4×) with brine, dried and evaporated. The residue was triturated with Et$_2$O and filtered to afford the title product as a white solid; m.p. 131°–133° C.

Step 2: 6-[4-(4-hydroxy)tetrahydropyranyl]pyridin-2-ylmethanol

To a solution of the bromo derivative from Step 1 (7.7 g) in THF (50 mL) and Et$_2$O (150 mL), cooled to 0° C., there was slowly added n-BuLi 2M in hexanes (30 mL) affording a red-brown suspension. An inlet tube above the surface of the mixture was connected to a flask in which paraformaldehyde (25 g) was gently heated at 175° C. to generate formaldehyde. When all the paraformaldehyde had been decomposed, to the reaction mixture was added saturated aqueous NH$_4$Cl (100 mL) and EtOAc (500 mL). The organic phase was washed (4×) with brine, dried and evaporated to a residue which was chromatographed on silica gel, eluting with EtOAc to afford the title product as a thick yellow oil.

Alcohol 7:
6-[4-(4-Methoxy)tetrahydropyranyl]pyridin-2-ylmethanol

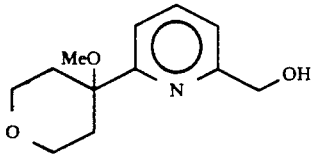

Step 1: 2-Bromo-6-[4-(4-methoxy)tetrahydropyranyl]pyridine

To a suspension of KH (35% dispersion in oil, 1.25 g) in THF (75 mL), cooled to 0° C., there was added 2-bromo-6-[4-(4-hydroxy)tetrahydropyranyl]pyridine from Alcohol 6, Step 1. When gassing had subsided, the mixture was warmed to r.t. and a thick suspension resulted. To this was added methyl iodide (1.71 g) and the resulting suspension was stirred at r.t. for 30 min. The THF was evaporated away, and the residue was partitioned between H$_2$O and EtOAc. The residue from evaporation of the organic phase was triturated with hexane and filtered to afford the product as a white solid; m.p. 69°–71° C.

Step 2: 6-[4-(4-Methoxy)tetrahydropyranyl]pyridin-2-ylmethanol

Following the procedure described in Alcohol 6, Step 2, but substituting the bromo derivative from Step 1 for 2-bromo-6-[4-(4-Hydroxy)tetrahydropyranyl]pyridine, the title product was obtained as a white solid; m.p. 84°–86° C.

Alcohol 8:
4-[4-(4-Hydroxy)tetrahydropyranyl]pyridin-2-ylmethanol

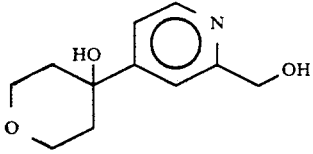

Following the procedure described in Alcohol 5, Steps 1–3, but substituting 4-bromopyridin-2-ylmethanol (Chem. Pharm. Bull. 1990, 38, 2446) for 5-bromo-pyridin-3-yl methanol as starting material, the title product was obtained as a white solid.

Alcohol 9:
[1S,5R]-5-[3-(3α-Hydroxy-6,8-dioxabicyclo[3.2.1]octanyl)]pyridin-3-ylmethanol

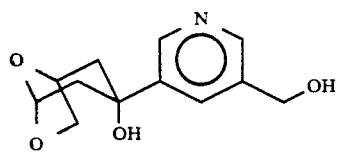

Following the procedure described in Alcohol 5, Steps 2–3, but substituting [1S,5R] 6,8-dioxaicyclo[3.2.1]octan-4-one from Alcohol 4, Step 3, for tetrahydro-4H-pyran-4-one, the title product was obtained as a white solid.

Alcohol 10:
[1S,5R]-6-[3-(3α-Hydroxy-6,8-dioxabicyclo[3.2.1]octanyl)]pyridin-2-ylmethanol

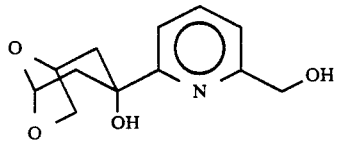

Step 1: 6-Bromo-O-tert-butyldiphenylsilypyridin-2-ylmethanol

Following the procedure described in Alcohol 5, Step 1, but substituting 6-bromopyridin-2-ylmethanol (Chem. Pharm. Bull., 1990, 38, 2446) for 5-bromopyridin-3-ylmethanol, the title product was obtained as a colorless oil.

Step 2: [1S, 5R]-6-[3-(3α-Hydroxy-6,8-dioxabicyclo[3.2.1]octanyl)]pyridin-2-ylmethanol Following the procedure described in Alcohol 5, Steps 2–3, but substituting 6-bromo-O-tert-butyldiphenylsilylpyridin-2-ylmethanol from Step 1 for 5-bromo-O-tert-butyldiphenylsilylpyridin-3-ylmethanol, and substituting [1S, 5R] 6,8-dioxabicyclo [3.2.1]octan-4-one from Alcohol 4, Step 3, for tetrahydro-4H-pyran-4-one, the title product was obtained as a white solid.

Alcohol 11:
2-[4-(4-Hydroxy)tetrahydropyranyl]pyridin-4-ylmethanol

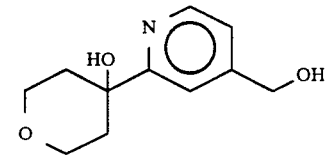

Following the procedure described in Alcohol 5, Steps 1–3, but substituting 2-bromopyridin-4-ylmethanol (Chem. Pharm. Bull. 1990, 38, 2446) for 5-bromo-pyridin-3-ylmethanol as starting material, the title product was obtained as a white solid.

Alcohol 12: [1S, 5R]
5-Fluoro-3-[3-(3α-hydroxy-6,8-dioxabicyclo[3.2.1]octanyl)]phenol

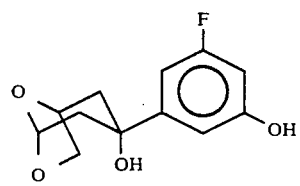

Step 1: 2,4-Di-O-p-toluenesulfonyl-1,6-anhydro-β-D-glucose

To a solution of 1,6-anhydro-β-D-glucose (50 g, 308 mmoL) in dry pyridine (100 mL) at 0° C. was added dropwise a solution of p-toluenesulfonyl chloride (123 g, 647 mmoL) dissolved in CHCl$_3$ (350 mL) and pyridine (200 mL). The reaction mixture was stirred at r.t. for at least 2 days. Water was added and the reaction mixture was stirred for approx. 1 hr. then the organic layer was decanted and the aqueous phase was reextracted with CHCl₃. The combined organic layers were washed with H₂SO₄ (10%) until the pH remained acidic, then finally washed with a saturated NH₄OAc solution. The resulting organic layer was dried over MgSO₄ and the solvent evaporated. The syrup obtained was flash chromatographed on silica gel eluting with hexane:EtOAc (1:1) to give the title compound as an oil.

Step 2: [1S, 3S, 5R] 6,8-Dioxabicyclo[3.2.1]octan-3-ol

The ditosylate derivative from Step 1 (107 g, 0.228 mmoL) was dissolved in THF (1.6 L) at −40° C. and Super-Hydride in THF (800 mL, 1M, 0.8 mmoL) was slowly added. The resulting reaction mixture was stirred at r.t. overnight. The reaction was cannulated into cold H₂O (226 mL) using external cooling, then NaOH 3N (640 mL, 1.92 mmoL) and H₂O₂ (30%) (490 mL, 4.3 mmoL) were successively added. The reaction was stirred at r.t. for 1 hr. Then the supernatant (THF layer) was separated from the aqueous layer and concentrated. The resulting residue was combined with the aqueous layer and extracted with CH₂Cl₂ using a continuous extractor. The organic layer was dried (MgSO₄) and evaporated to dryness. The oily residue was dissolved in hot Et₂O, filtered and evaporated to dryness affording the title compound contaminated with the 2-octanol isomer. The crude product was used as such for the next step.

Step 3: [1S, 5R] 6,8-Dioxabicyclo[3.2.1]octan-3-one

The crude alcohol from Step 2 (16.6 g, 89 mmoL) in CH₂Cl₂ (200 mL) was added slowly to a suspension of PCC (38.4 g, 178 mmoL) and celite (22 g) in CH₂Cl₂ (400 mL) and stirred for 1 hr. The reaction mixture was diluted with Et₂O (600 mL) and &iltered over celite. The filtrate was evaporated and the residue distilled with a Kügelrohr apparatus (10° C., 1.8 mm/Hg) affording the title product as an oil.

Step 4: [1S, 5R] O-Benzyl-3-[3-(3α-hydroxy-6,8-dioxabicyclo[3.2.1]octanyl)]-5-fluorophenol To a solution of O-benzyl-3-bromo-5-fluorophenol (1.03 g, EP 385,662) in THF (15 mL) stirred at −78° C. was added a solution of n-BuLi in hexane (2.5M, 1.62 mL). After 1 hr. a solution of [1S, 5R] 6,8-dioxabicyclo[3.2.1]octan-3-one (471 mg) from Step 3 in THF (2 mL) was added dropwise to the resulting mixture. After 45 min. at −78° C., the reaction mixture was stirred at 0° C. for 1 hr. Saturated aqueous NH₄Cl was then added and the organic phase separated. The aqueous phase was extracted was EtOAc (3×) and the combined organic phases were washed with brine, dried (MgSO₄), and evaporated to afford the title product as an oil.

Step 5: [1S, 5R] 5-Fluoro-3-[3-(3α-hydroxy-6,8-dioxabicyclo[3.2.1]octanyl)]phenol A mixture of O-benzylphenol derivative (1.1 g) from Step 4, Pd/C (10%) (100 mg) in EtOH (20 mL) was stirred over H₂ (1 Atm.) for 1 hr. Then, CH₂Cl₂ (20 mL) was added and the resulting mixture was filtered over celite. The filtrate was evaporated and the crude product was flash chromatographed on silica gel eluting with EtOAc/hexane (3:2) to afford the title product as a white solid.

PREPARATION OF NAPHTHOLS

Naphthol 1: 1-Phenyl-3-carboxy-6-naphthol

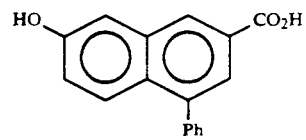

Method A (Scheme I):

Step 1: 4-Hydroxy-2-(3-methoxybenzylidene)-4phenylbut-3-enoic acid lactone

A mixture of 4-phenyl-4-oxobutanoic acid (52 g), m-anisaldehyde (47.6 g), sodium acetate (24 g) and acetic anydride (177.5 g) was stirred and heated at 70° C. for 8 hr. After cooling down to r.t., the resulting yellow slurry was diluted with H₂O (1 L) and after stirring for 15 min. the supernatant was decanted. The solids were washed in the same manner with H₂O (3×), then filtered and washed well with H₂O. The yellow-orange solid, still clamped, was used as such in the next step.

Step 2: 1-Phenyl-3-carboxy-6-methoxynaphthalene

The crude, lactone from Step 1 was suspended in glacial AcOH (750 mL) and 37% HCl (750 mL), and the mixture was refluxed for 2.5 hr. After cooling down to r.t., H₂O (1.5 L) was added, the mixture was stirred for 15 min. and the supernatant was decanted. The solid was again stirred with H₂O (2 L) and filtered, washed copiously with H₂O and dried under vacuum. This solid was stirred in a 1:1 mixture of Et₂O and hexane (500 Ml) for 2 hr. and filtered to afford the desired naphthoic acid as a beige solid.

Step 3: 1-Phenyl-3-carboxy-6-naphthol

The acid from Step 2 (55 g) and pyridine.Hcl (400 g) were heated together at 175° C. for 10 hr. After cooling to r.t., H₂O (2 ) was added, and after stirring for 15 min., the mixture was filtered. The solid was dissolved in H₂O (1.5 ) and 10N aqueous NaOH (35 Ml), the solution was filtered and the filtrate acidified with 1N aqueous Hcl. The resulting precipitate was filtered, washed copiously with H₂O and dried to afford the desired naphthol as a tan solid.

Naphthol 2: 1-(3-Furyl)-3-carboxy-6-naphthol

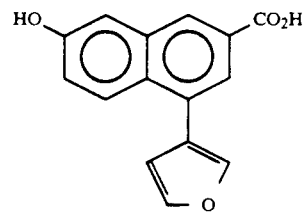

Step 1: Ethyl 4-(3-furyl)-4-oxobutanoate

Under N₂, 3-furoic acid (25 g, 0.223 mmoL) was dissolved in CH₂Cl₂ (200 mL) and DMF (few drops) then oxalyl chloride (23.9 mL, 0.267 mmoL) was added at 0° C. The resulting solution was stirred at 0° C. for 15 min. and at r.t. for 30 min. The solvent was evaporated and replaced by dry benzene (200 mL) for the addition. In a separate flask, the ethyl 3-iodopropionate (73.25 g, 0.334 mmoL) was dissolved in dry benzene (400 mL) then dimethylacetamide (45 mL) and Zn-Cu (32 g, 0.512 mmoL) were added. The mixture was stirred at r.t. for 1 hr. and at 60° C. for 3 hr. The (Ph₃P)₄Pd° (10.25 g, 8.87 mmoL) was added and the reaction was stirred at the same temperature for 5 min. The oil bath was removed and the solution of acyl chloride in benzene was added all at once. The resulting mixture was stirred for 30 min., diluted with EtOAc, washed successively with HCl 1N (2×), saturated NaHCO₃ and brine, dried over MgSO₄, filtered and evaporated. The crude residue was purified by chromatography on silica gel eluting with hexane:EtOAc (9:1) to afford the title product as a white solid.

Step 2: 4-(3-Furyl)-4-oxobutanoic acid

The keto ester from Step 1 (38.9 g, 0.193 mmoL) was dissolved in a mixture of MeOH:H₂O:THF (3:1:2) (150 mL) and NaOH 1N (213 mL, 0.213 mmoL) was added. The reaction was stirred at r.t. overnight. The mixture was concentrated, acidified with HCl 1N extracted (2×) with EtOAc, washed with brine, dried over MgSO₄, filtered and evaporated to afford the title product as a beige solid.

Step 3: 1-(3-Furyl)-3-carboxy-6-naphthol

Following the procedure described in Naphthol 1, Steps 1-3, but substituting 4-(3-furyl)-4-oxobutanoic acid from Step 2 for 4-phenyl-4-oxobutanoic acid, the title product was obtained as a beige solid.

Naphthol 3:
1-(2-Thienyl)-3-cyano-6-hydroxynaphthalene

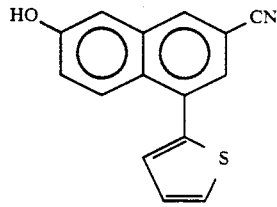

Method B (Scheme II):

Step 1: 3-Carbethoxy-4-(3-benzyloxyphenyl)-3(Z)butenoic acid

To a solution of LiOMe in MeOH (2.7M, 450 mL) was added dropwise a mixture of 3-benzyloxybenzaldehyde (100 g, 0.47 mmoL) and diethylsuccinate (123 g, 0.71 mL). The reaction mixture was refluxed for 16 hr., cooled to r.t. and the solvent evaporated. The residue was acidifed to pH 2 with HCi 50% and extracted with EtOAc (800 mL). The organic phase was washed with H₂O (3×) then extracted with a saturated NaHCO₃ solution. The basic extracts were acidified to pH 2 with HCl 6N and extracted with EtOAc (3×250 mL). The organic phase was washed with brine, dried over MgSO₄ and evaporated to afford the title compound as an oil.

Step 2: 1-Trifluoroacetyl-3-carbomethoxy-6-benzyloxynaphthalene

To a solution of the corresponding acid from Step 1 (71 g, 0.22 mmoL) in TFAA (270 mL) and CH₂Cl₂ (70 mL) was added portionwise at −10° C. NaOAc (36 g, 0.44 mmoL). The cooling bath was then removed and the reaction mixture was stirred at r.t. for 2 hr. The solvent was then evaporated and the residue was dissolved in EtOAc, washed a few times with saturated solution of NaHCO₃, brine and the solvent evaporated to afford the title compound as an oil.

Step 3: 1-Hydroxy-3-carbomethoxy-6-benzyloxynaphthalene

The trifluoroacetoxy derivative from Step 2 was dissolved in MeOH (300 mL) and K₂CO₃ (30 g, 0.22 mmoL) was added portionwise. The resulting reaction mixture was stirred for 16 hr. then transferred to a solution of HCl 1N, extracted with EtOAc. The combined organic phases were washed successively with H₂O, brine, dried over MgSO₄ and evaporated. Purification by flash chromatography (hexanes:EtOAc; 4:1) gave the title compound as an oil.

Step 4: 1-Trifluoromethanesulfonyl-3-carbomethoxy-6-benzyloxynaphthalene

To a solution of the alcohol from Step 3 (410 mg, 1.3 mmoL) in CH₂Cl₂ (20 mL) was added Et₃N (0.2 mL, 1.6 mmoL) and at 0° C. trifluoromethanesulfonic anhydride (0.25 mL, 1.55 mmoL). The reaction mixture was stirred for 3 hr., diluted with CH₂Cl₂, washed successively with HCl 1N, brine, dried over MgSO₄ and evaporated. Purification by flash chromatography (hexanes:EtOAc; 85:15) gave the title compound as an oil.

Step 5: 1-(2-Thienyl)-3-carbomethoxy-6-benzyloxynaphthalene

To a solution of 2-bromothiophene (579 mg, 3.6 mmoL) in dry THF (10 mL) was added at −78° C. n-BuLi in hexane (1.8 mL, 3.6 mmoL, 1.96M). The resulting solution was stirred for 1 hr., then (MeO)₃B (0.4 mL, 3.6 mmoL) was added dropwise and after 30 min., a mixture of the corresponding triflate from Step 4 in THF (6 mL) and H₂O (2 mL) containing (Ph₃P)₄Pd (340 mg, 0.3 mmoL) was added. The cooling bath was removed and the resulting mixture was heated to 60° C. for 1 hr. The solvent was evaporated and H₂O was added followed by extraction with EtOAc. The combined organic phases were washed successively with H₂O, brine, dried over MgSO₄ and evaporated. Purification by flash chromatography (toluene:EtOAc; 99.5:0.5) gave the title compound as a solid.

Step 6: 1-(2-Thienyl)-3-cyano-6-benzyloxynaphthalene

To a suspension of the ester from Step 5 (420 mg, 1.1 mmoL) in toluene (10 mL) was added a solution of dimethylaluminium amide (1M, 3.4 mL, 3.4 mmoL). The mixture was refluxed for 16 hr., then transferred to a solution of HCl 1N and extracted with EtOAc. The combined organic phases were washed with brine, dried over MgSO₄, and evaporated. The crude product was then dissolved in THF (8 mL) and TFAA (0.5 mL, 3.4 mmoL) was added at 0° C. The cooling bath was removed and the reaction mixture was stirred at r.t. for 2 hr. Water was added and the mixture was extracted with EtOAc. The combined organic phases were washed successively with H₂O, brine, dried over MgSO₄, and evaporated to afford the title compound as an oil.

Step 7: 1-(2-Thienyl)-3-cyano-6-hydroxynaphthalene

To a solution of the crude benzyloxy naphthalene derivative from Step 6, in thioanisole (2 mL) and TFA (6 mL) was heated at 65° C. for 1 hr. Then the solvent was evaporated and the resulting mixture was applied onto a flash chromatography column and eluted with hexanes:EtOAc (95:5) to give the title compound as a solid.

Naphthol 4:
1-(3-Thienyl)-3-cyano-6-hydroxynaphthalene

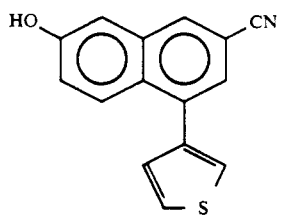

Following the procedure described in Naphthol 3, Steps 5-7, but substituting 3-bromothiophene for 2-bromothiophene and Et$_2$O for THF, the title product was obtained as a white solid.

Naphthol 5:
1-(2-Thiazolyl)-3-carbomethoxy-6-naphthol

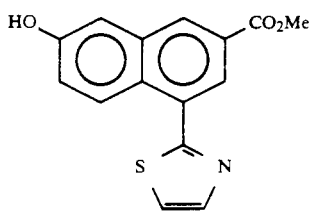

Method C (Scheme III):

Step 1: 3-Carbethoxy-4-(3-methoxyphenyl)-3(Z)-butenoic acid

To a solution of LiOEt in EtOH (1.92M, 450 mL) at reflux was added dropwise a mixture of m-anisaldehyde (90 g) and diethyl succinate (150 g). The reaction was acidified to pH 2 with HCl 50% and extracted with EtOAc (800 mL). The organic phase was washed with H$_2$O (3×) then extracted with saturated to pH 2 with HCl 6N and extracted with EtOAc (3×, 250 mL). The organic phase was washed with brine, dried over MgSO$_4$ and evaporated to afford the title compound as an oil.

Step 2: 3-Carbethoxy-4-(3-methoxyphenyl)butanoic acid

A solution of mono acid from Step 1 (115 g) in AcOH (320 mL) containing Pd/C 10% (4 g) was hydrogenated (Parr, 20 psi) for 5 hr. The reaction mixture was filtered and the solvent evaporated to afford the title compound as an oil.

Step 3: 3-Carbethoxy-6-methoxy-1-tetralone

To a mixture of mono acid from Step 2 (30 g) and NaOAc (20 g) at 0° C. was added TFAA (100 mL) dropwise (over 3 hr. period). The reaction mixture was stirred 3 hr. at r.t. then poured into crushed ice, neutralized with NaOH 6N, extracted with EtOAc, washed with H$_2$O, brine, dried over MgSO$_4$ and evaporated. The residue was flash chromatographed, eluting with hexane:EtOAc (80:20→75:25) to afford the title compound as an oil.

Step 4: 1-(2-Thiazolyl)-3-carbethoxy-6-methoxy-1,2,3,4-tetrahydro-1-naphthol

To a solution of thiazole (428 mL, 6.04 mmoL) in Et$_2$O (20 mL) was added at −78° C. dropwise a solution of n-BuLi in hexanes (1.96M, 3.08 mL) and the solution was stirred for 30 min. A solution of keto ester from Step 3 (1 g, 4.02 mmoL) in Et$_2$O (2 mL) was then added dropwise and the reaction was stirred at −78° C. for 1 hr. and warmed to r.t. A saturated NaHCO$_3$ solution was added and the mixture was extracted with Et$_2$O (2×), washed with H$_2$O, dried over MgSO$_4$, filtered and evaporated. The crude compound was purified by flash chromatography on silica gel (hexanes:EtOAc; 7:3) to afford as a yellow oil a mixture of the title alcohol and the lactone resulting from a loss of EtOH.

Step 5: 1-(2-Thiazolyl)-3-carbethoxy-6-methoxy-3,4-dihydronaphthalene

To the mixture of alcohol ester and lactone from Step 4 (490 mg, 1.47 mmoL) in benzene (20 mL) was added CSA (273 mg, 1.47 mmol) and the resulting mixture was refluxed with a Dean Stark for 16 hr. The solution was diluted with EtOAc, washed successively with saturated NaHCO$_3$ and H$_2$O, dried over MgSO$_4$ and evaporated to afford the title product as a brown oil.

Step 6: 1-(2-Thiazolyl)-3-carbethoxy-6-methoxynaphthalene

To a solution of the dihydronaphthalene derivative from Step 5 (407 mg, 1.47 mmoL) in benzene (20 mL) was added DDQ (334 mg, 1.47 mmoL). After 5 min., the solvent was evaporated and the crude material was purified on silica gel column eluting with EtOAc:hexane (3:7) to afford the title product as a dark oil.

Step 7: 1-(2-Thiazolyl)-3-carboxy-6-naphthol

Following the procedure described in Naphthol 1, Step 3, but substituting 1-(2-thiazolyl)-3-carbethoxy-6-methoxynaphthalene from Step 6, for 1-phenyl-3-carboxy-6-methoxynaphthalene, the title product was obtained and used as such for the next step.

Step 8: 1-(2-Thiazolyl)-3-carbomethoxy-6-naphthol

To a solution of the acid from Step 7 (108 mg, 0.4 mmoL) in EtOAc (20 mL) was added an excess of CH$_2$N$_2$ in Et$_2$O. After 5 min., the solution was evaporated to afford the title compound as an orange oil.

Naphthol 6:
1-(5-Thiazolyl)-3-carbomethoxy-6-naphthol

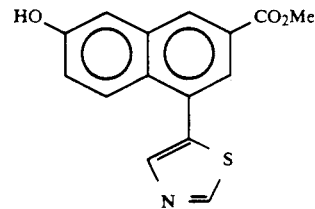

Step 1: 1-(5-Thiazolyl)-3-carbethoxy-6-methoxy-1,2,3,4-tetrahydro-1-naphthol

To a solution of 2-trimethylsilylthiazole (2.2 g, 13.9 mmoL) (J. Org. Chem., 1988, 53, 1748) in Et$_2$O (12 mL) was added at −78° C., dropwise a solution of n-BuLi in hexanes (2.45m, 5.68 mL) and the solution was stirred for 30 min. A solution of keto ester from Naphthol 5, Step 3, (2.0 g, 8.05 mmoL) in Et$_2$O (5 mL) was then added dropwise and the reaction was stirred at −78° C. for 1 hr. and warmed to r.t. A saturated NaHCO$_3$ solution was added and the mixture was extracted with Et$_2$O (2×), washed with H$_2$O, dried over MgSO$_4$, filtered and evaporated. The crude compound was purified by flash chromatography on silica gel eluting with hexanes: EtOAc (7:3) to afford directly the title alcohol as an oil.

Step 2: 1-(5-Thiazolyl)-3-carbomethoxy-6-naphthol

Following the procedure described in Naphthol 5, Steps 5–8, but substituting 1-(5-thiazolyl)-3-carbethoxy-6-methoxy-1,2,3,4-tetrahydro-1-naphthol from Step 1, for 1-(2-thiazolyl)-3-carbethoxy-6-methoxy-1,2,3,4-tetrahydro-1-naphthol, the title product was obtained as an orange solid.

Naphthol 7: 1-Phenyl-6-naphthol

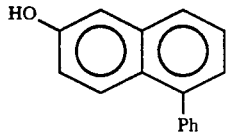

A mixture of 1-phenyl-3-carboxy-6-naphthol (Naphthol 1, 250 mg) and copper powder (125 mg) in quinoline (6 mL) was heated at 225° C. for 3.5 hr. The cooled mixture was diluted with EtOAc, washed twice with 1N aqueous HCl, then with $H_2O$, aqueous $NaHCO_3$ and again $H_2O$, dried and evaporated. The residue was chromatographed on silica gel, eluting with a 1:3 mixture of EtOAc and hexane, to afford the final naphthol as an oil which solidified to a light brown solid.

Naphthol 8: 1-Phenyl-3-acetyl-6-naphthol

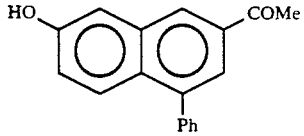

To a solution of 1-phenyl-3-carboxy-6-naphthol (Naphthol 1) (12 g) in $Et_2O$ (150 mL) at 0° C. was added MeLi in $Et_2O$ (1.4M, 160 mL) dropwise (over 45 min. period). The reaction mixture was stirred at r.t. for 24 hr., quenched with TMSCl until pH ~ 1, then $H_2O$ was added (100 mL). After 2 hr. with vigorous stirring, the organic phase was separated, washed with $H_2O$, saturated $K_2CO_3$ solution (3×), brine, dried over $MgSO_4$ and evaporated. The solid was treated with $Et_2O$ and filtered to afford the title compound as beige solid.

Naphthol 9: 1-Phenyl-3-pentanoyl-6-naphthol

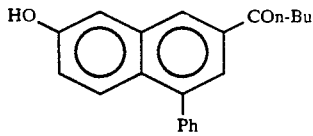

Following the procedure described in Naphthol 8, but substituting n-BuLi for MeLi, the title compound was obtained as a cream solid.

Naphthol 10: 1-Phenyl-3-ethyl-6-naphthol

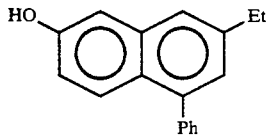

To a solution of 1-phenyl-3-acetyl-6-naphthol (Naphthol 8) (300 mg) in EtOAc was added $Pd(OH)_2/C$ (20%, 50 mg) and stirred under $H_2$ (balloon) for 24 hr.

The mixture was filtered on celite and the filtrate evaporated. The residue was flash chromatographed, eluting with hexanes: $EtOAc:CH_2Cl_2$ (9:1:5) to afford the title compound.

Naphthol 11: 1-Phenyl-3-carbomethoxy-6-naphthol

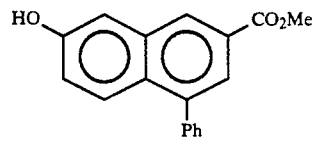

To a suspension of 1-phenyl-3-carboxy-6-naphthol (Naphthol 1) (5 g) in MeOH (60 mL) there was added dropwise thionyl chloride (1.52 mL). The mixture was stirred at r.t. overnight affording a red solution. The MeOH was evaporated and the residue was chromatographed on silica gel, eluting with a 1:1 mixture of EtOAc and hexanes, to afford the ester as a tan solid.

Naphthol 12: 1-(3-Furyl)-3-carbomethoxy-6-naphthol

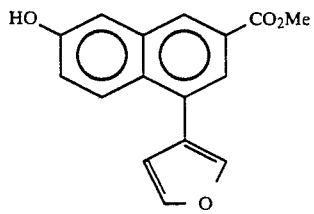

To a solution of 1-(3-furyl)-3-carboxy-6-naphthol (Naphthol 2) (50 g) in MeOH (300 mL) was bubbled HCl (g) for 10 min. The reaction mixture was stirred at r.t. for 1 hr., then 70° C. for 3 hr. the solvent was evaporated and the residue dissolved in EtOAc, washed with $H_2O$, saturated $NH_4Cl$ solution, brine, dried over $MgSO_4$ and the solvent evaporated to afford the title compound as a pale yellow solid.

Naphthol 13: 1-Phenyl-3-cyano-6-naphthol

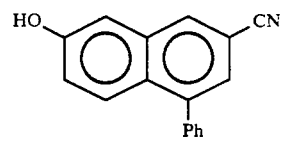

To a suspension of 1-phenyl-3-carbomethoxy-6-naphthol (Naphthol 11) (890 mg, 3.19 mmoL) in toluene (50 mL) was added dimethylaluminum amide (1M, 9.59 mmoL), 9.59 mL). The mixture was heated at reflux for 16 hr. At 0° C., HCl 1N (excess) was carefully added and the mixture was stirred at 0° C. for 15 min., then extracted (2×) with $CH_2Cl_2$. A precipitate (1) was filtered from the extracts. The organic phase was washed with brine, dried over $MgSO_4$, filtered and evaporated to give a white solid (2). Precipitate 1 was stirred in EtOAc for 30 min., filtered and the filtrate was evaporated. The residue was dissolved in dioxane (5 mL) and pyridine (969 μL, 12 mmoL) was added and the solution was cooled at 0° C. Then TFAA (867 μL, 6 mmoL) was added, the ice bath was removed and the mixture was stirred at r.t. for 1 hr. Water was added to the reaction and the solution was extracted (2×) with EtOAc, washed with brine, dried and evaporated to give a solid (3). The crude compound (2+3) was purified by flash chromatography using EtOAc:hexane (7:3) as eluent. The title compound was then obtained as a yellow solid.

Naphthol 14: 1-(3-Furyl)-3-cyano-6-naphthol

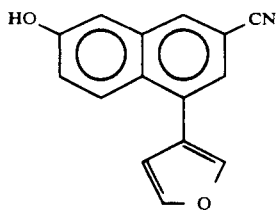

Following the procedure described in Naphthol 13, but substituting 1-(3-furyl)-3-carbomethoxy-6-naphthol (Naphthol 12) for 1-phenyl-3-carbomethoxy-6-naphthol, the title product was obtained as a solid; m.p. 194°–195° C.

Naphthol 15: 1-(3-Furyl)-3-formyl-6-naphthol

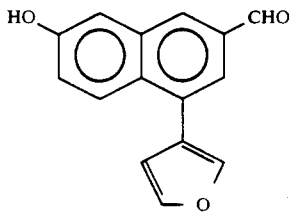

To a solution of 1-(3-furyl)-3-cyano-6-naphthol (Naphthol 14) (1.5 g) in THF (30 mL) at −78° C. was added DIBAL-H in toluene (1.5M, 9.3 mL) dropwise. The reaction mixture was warmed to r.t., stirred for 1 hr., cooled to 0° C., quenched with HCl 10% dropwise and diluted with EtOAc. The organic phase was separated, washed with H$_2$O, brine, dried over MgSO$_4$ and the solvent evaporated to afford the title compound as a foam.

Naphthol 16: 1-Phenyl-3-methylthioacetyl-6-naphthol

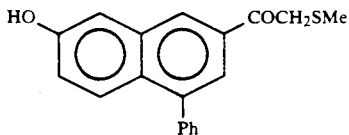

Step 1: 1-Phenyl-3-carbomethoxy-6-benzyloxynaphthalene

Following the procedure described in Naphthol 3, Step 5, but substituting bromobenzene for 2-bromothiophene, the title compound was obtained.

Step 2: 1-Phenyl-3-carboxy-6-benzyloxynaphthalene

Following the procedure described in Naphthol 2, Step 2, but substituting 1-phenyl-3-carbomethoxy-6-benzyloxynaphthalene from Step 1, for ethyl 4-(3-furyl)-4-oxobutanoate, the title compound was obtained.

Step 3: 1-Phenyl-3-chloroacetyl-6-benzyloxynaphthalene

To a solution of acid from Step 2, (1.5 g) in CH$_2$Cl$_2$ (50 μL) was added oxalyl chloride (700 mL). The reaction mixture was stirred at r.t. for 6 hr. and the solvent evaporated. The residue was dissolved in Et$_2$O (20 mL), an excess of CH$_2$N$_2$ in Et$_2$O was added. After 1 hr. at r.t., HCl (gas) was bubbled for 10 min. through the reaction mixture. The mixture was then diluted with Et$_2$O, washed with H$_2$O (2×), pH 7 buffer solution, brine, dried over MgSO$_4$ and the solvent evaporated. The residue was flash chromatographed, eluting with hexane:EtOAc:CH$_2$Cl$_2$ (95:5:30) to afford the title compound as a pale yellow solid.

Step 4: 1-Phenyl-3-methylthioacetyl-6-benzyloxynaphthalene

A mixture of chloroacetyl derivative from Step 3 (150 mg), Cs$_2$CO$_3$ (75 mg), thioacetic acid (30 μL) in EtOH (10 mL) was stirred at r.t. for 1 hr. The reaction mixture was diluted with Et$_2$O, washed with pH 7 buffer solution, brine and the solvent evaporated. The residue was dissolved in MeOH, NaOMe (1M, 3 drops) and MeI (50 μL) was added. The mixture was stirred at r.t. for 3 hr. and diluted with a saturated NH$_4$Cl solution and Et$_2$O. The organic phase was separated, washed with H$_2$O, brine, dried over MgSO$_4$ and the solvent evaporated. The residue was flash chromatographed, eluting with hexane:EtOAc (85:15) to afford the title compound as a foam.

Step 5: 1-Phenyl-3-methylthioacetyl-6-naphthol

A solution of methylthioacetyl derivative from Step 4 (140 mg) in AcOH (1 mL) and conc. HCl (1 mL) was stirred at r.t. 18 hr. The reaction mixture was diluted with Et$_2$O, washed with H$_2$O (2×), saturated NaHCO$_3$ solution, brine, dried over MgSO$_4$ and the solvent evaporated. The residue was flash chromatographed, eluting with hexane:EtOAc:CH$_2$Cl$_2$ (85:15:50) to afford the title compound as a foam.

Naphthol 17: 1-Phenyl-3-phenylthiomethyl-6-naphthol

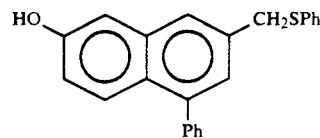

Step 1: 1-Phenyl-3-hydroxymethyl-6-naphthol

To a solution of 1-phenyl-3-carbomethoxy-6-naphthol (Naphthol 11) (2.5 g, 9 mmoL) in dry THF (50 mL) at 0° C. was added (4.8 mL, 2.7 mmoL, 3 eq.) of DIBAL-H. The resulting solution was stirred for 2 hr. Then methanol (excess) was added and the solvent evaporated. The mixture was diluted with EtOAc, washed successively with HCl, 1N, H$_2$O, brine, to give the title compound.

Step 2: 1-Phenyl-3-chloromethyl-6-naphthol

To a solution of the alcohol from Step 1 (1.46 g, 5.8 mmoL) in CH$_2$Cl$_2$ (50 mL) was added CCl$_4$ (5.7 mL, 58 mmoL, 10 eq.) followed by Ph$_3$P (3 g, 11.7 mmoL, 2 eq.). The resulting mixture was refluxed for 2 hr. The solvent was evaporated and a purification by flash chromatography on silica gel (hexanes: EtOAc; 8:2) gave the title compound.

Step 3: 1-Phenyl-3-phenylthiomethyl-6-naphthol

To a solution of the halide from Step 2 (600 mg, 0.22 mmoL) in dry DMF (5 mL) was added at r.t. NaH (90 mg, 2.2 mmoL), followed by thiophenol (114 mL, 1.1 mmoL). The reaction mixture was stirred at r.t. for 18 hr., then transferred to H$_2$O and extracted with EtOAc. The combined organic phases were washed with brine, and dried over MgSO4. After evaporation of the solvent and purification by flash chromatography on silica gel (hexanes:EtOAc; 7:3) the title compound was obtained.

Naphthol 18: 1-Phenyl-3-dimethylcarboxamido-6-naphthol

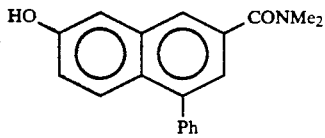

A mixture of 1-phenyl-3-carbomethoxy-6-naphthol (Naphthol 11) (125 mg) in toluene (10 mL) and dimethylaluminum dimethylamine (Me2AlNMe2) in toluene 0.2M (5 mL) was heated to 85° C. for 5 hr. The mixture was cooled to r.t., diluted with EtOAc, washed with saturated NH4Cl solution, brine, dried over MgSO4 and the solvent evaporated. The solid residue was treated with Et2O and filtered to afford the title compound as a white solid.

Naphthol 19: 1-(3-Furyl)-2-cyano-6-naphthol

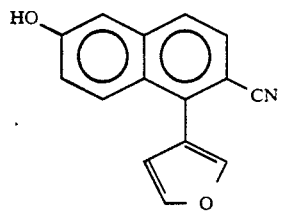

Step 1: 2-(α-Hydroxybenzyl)-5-benzyloxybenzaldehyde dimethylacetal

To a solution of 2-bromo-5-benzyloxybenzaldehyde dimethylacetal (Tet. Lett., 22, 5027 (1981)) (130 g) in THF (2.0 L), cooled to −78° C., was added dropwise a solution of n-BuLi (210 ml, 1.91M) in hexane. After 15 min., a solution of 3-furaldehyde (26.7 mL) in THF (50 ml) was added dropwise. The cooling bath was removed, then the reaction mixture was warmed slowly (40 min.) to −10° C. and quenched with a saturated NH4Cl solution. The reaction mixture was diluted with Et2O (2.0 L). The organic phase decanted, washed with H2O (3×), brine, dried over MgSO4, and the solvents evaporated. The residue was chromatographed on silica gel (hexane/EtOAc 95:5 to 85:15) to give the title product as a foam.

Step 2: 1-(3-Furyl)-2-cyano-6-benzyloxynaphthalene

To a solution of alcohol from Step 1 (200 mg) in chlorobenzene (20 mL), was added acrylonitrile (800 μL) and trifluoroacetic acid (100 μL). The reaction mixture was heated to reflux for 6 hr, then cooled to r.t. The solvent was evaporated and the resulting residue was flash chromatographed on silica gel (hexane: EtOAc, 85:15) to afford the title product as a yellow solid.

Step 3: 1-(3-Furyl)-2-cyano-6-naphthol

Following the procedure described in Naphthol 3, Step 7, but substituting 1-(3-furyl)-2-cyano-6-benzyloxynaphthalene for 1-(2-thienyl)-3-cyano-6-benzyloxynaphthalene, the title product was obtained.

Naphthol 20: 1-(3-Furyl)-3-acetyl-6-naphthol

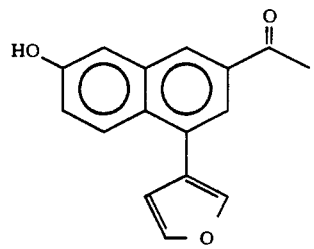

Following the procedure described in Naphthol 8, but substituting 1-(3-furyl)-3-cyano-6-naphthol (Naphthol 14) for 1-phenyl-3-carboxy-6-naphthol (Naphthol 1), the title product was obtained as a solid.

Naphthol 21: 1-(5-Pyrimidinyl)-3-carbomethoxy-6-naphthol

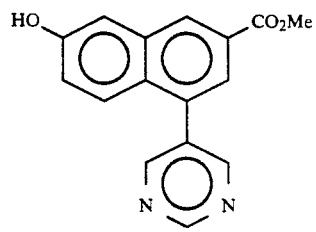

Step 1: 1-(5-Pyrimidinyl)-3-carbomethoxy-6-methoxynaphthalene

Following the procedure described in Naphthol 3, Step 5, but substituting 5-bromopyrimidine for 2-bromothiophene and 1-trifluoromethanesulfonyl-3-carbomethoxy-6-methoxynaphthalene for 1-trifluoromethanesulfonyl-3-carbomethoxy-6-benzyloxynaphthalene, the title compound was obtained.

Step 2: 1-(5-Pyrimidinyl)-3-carbomethoxy-6-naphthol

Following the procedure described in Naphthol 1, Step 3, but substituting 1-(5-pyrimidinyl)-3-carbomethoxy-6-methoxy-naphthalene for 1-phenyl-3-carboxy-6-methoxy naphthalene, the title product was obtained as a yellow solid.

Naphthol 22: 1-Cyano-3-carbomethoxy-6-naphthol

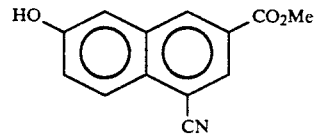

Step 1: 1-Cyano-3-carbethoxy-6-methoxy-1,2,3,4-tetrahydro-O-trimethylsilyl-1-naphthol To a solution of 3-carbethoxy-6-methoxy-1-tetralone from Naphthol 5, Step 3 (2 g, 7.0 mmoL) in CH2Cl2 (50 mL) at 0° C. was added TMSiCN (1.4 mL, 10.6 mmoL) followed by BF3.OEt2 (260 μL, 1.4 mmoL), and the reaction mixture was stirred at 0° C. for 15 min. and at r.t. for 1 hr. The resulting reaction mixture is then added to a saturated aqueous NaHCO3 solution, extracted with CH2Cl2, washed with brine, dried over MgSO4, and evaporated. The residue was flash chromatographed eluting with hexane: EtOAc (9:1→7:3) to afford the title compound.

Step 2: 1-Cyano-3-carbethoxy-6-methoxy-3,4-dihydro naphthalene

Following the procedure described in Naphthol 5, Step 5, but substituting the ester from Step 1 for the mixture of alcohol ester and lactone from Step 4 in Naphthol 5, the title compound was obtained and used as such for the next step.

Step 3: 1-Cyano-3-carbethoxy-6-methoxynaphthalene

Following the procedure described in Naphthol 5, Step 6, but substituting the ester from Step 2 for 1-(2-thiazolyl)-3-carbethoxy-6-methoxy-3,4-dihydronaphthalene, the title product was obtained as a white solid.

Step 4: 1-Cyano-3-carboxy-6-naphthol

Following the procedure described in Naphthol 1, Step 3, but substituting 1-cyano-3-carbethoxy-6-methoxynaphthalene from Step 3 for 1-phenyl-3-carboxy-6-methoxynaphthalene, the title compound was obtained as an orange solid.

Step 5: 1-Cyano-3-carbomethoxy-6-naphthol

Following the procedure described in Naphthol 5, Step 8, but substituting 1-cyano-3-carboxy-6-naphthol from Step 4 for 1-(2-thiazolyl)-3-carboxy-6-naphthol, the title product was obtained as an orange solid.

PREPARATION OF NAPHTHALENE INTERMEDIATE

Naphthalene 1:
1-Phenyl-3-hydroxymethyl-6-carbomethoxynaphthalene

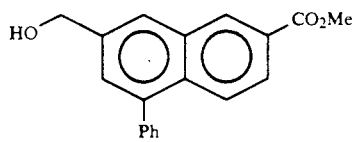

Step 1: 1-Phenyl-3-carbomethoxy-6-trifluoromethanesulfonyloxynaphthalene

Following the procedure described in Naphthol 3, Step 4, but substituting Naphthol 11 for 1-hydroxy-3-carbomethoxy-6-benzyloxynaphthalene, the title product was obtained.

Step 2: 1-Phenyl-3-hydroxymethyl-6-trifluoromethanesulfonyloxynaphthalene

Following the procedure described in Naphthol 17, Step 1, but substituting 1-phenyl-3-carbomethoxy-6-trifluoromethanesulfonyloxynaphthalene from Step 1 for 1-phenyl-3-carbomethoxy-6-naphthol, the title product was obtained.

Step 3: 1-Phenyl-3-hydroxymethyl-6-carbomethoxynaphthalene

To a solution of the alcohol from Step 2 (162 mg) in MeOH (2 mL) and DMSO (4 mL) was added triethylamine (130 μL), Pd(OAc)$_2$ (10 mg) and 1,1'-bis(diphenylphosphino)ferrocene (45 mg). Then carbon monoxide was bubbled through the resulting mixture for 10 min. Then an atmosphere of CO was maintained while the solution was heated to 70° C. for one hour. The reaction mixture was then allowed to cool to r.t. diluted with EtOAc washed successively with HCl 1N, saturated aqueous NaHCO$_3$, brine, dried and evaporated. Flash chromatography on silica gel (Hexane: EtOAc: 6:4) afforded the title compound.

The invention is further defined by reference to the following examples, which are intended to be illustrative and not limiting. All temperatures are in degrees Celsius.

EXAMPLE 1

1-Phenyl-3-carbomethoxy-6-[3-[4-(4-hydroxy)tetrahydropyranyl]benzyloxy]naphthalene A mixture of 3-[4-(4-hydroxy)tetrahydropyranyl]benzyl bromide (Halide 2) (1.5 g), 1-phenyl-3-carbomethoxy-6-naphthol (Naphthol 11) (1.24 g), and Cs$_2$CO$_3$ (1.9 g) in DMF (15 mL) was stirred at r.t. for 18 hr. To the reaction mixture was added H$_2$O (15 mL) followed by EtOAc (30 mL) and the organic layer decanted. The aqueous layer was extracted with EtOAc and the combined organic layers were washed with H$_2$O, brine, dried over MgSO$_4$ and evaporated. The residue was chromatographed on silica gel, eluting with hexane:EtOAc (80:20) to afford the title compound as a white solid; m.p. 98°-100° C.

EXAMPLE 2

1-Phenyl-3-carboxy-6-[3-[4-(4-hydroxy)tetrahydropyranyl]benzyloxy]naphthalene

To a solution of 1-Phenyl-3-carbomethoxy-6-[3-[4-(4-hydroxy)tetrahydropyranyl]benzyloxy]naphthalene (300 mg) (from Example 1) in a mixture of THF:MeOH:H$_2$O (3:1:1) (10 mL) was added LiOH.H$_2$O (50 mg). The reaction mixture was stirred at r.t. for 18 hr, then acidified to pH 3 with HCl 10% and diluted with Et$_2$O. The organic phase was separated, washed with H$_2$O, brine, dried over MgSO$_4$ and evaporated. The residue was flash chromatographed on silica gel, eluting with CH$_2$Cl$_2$:MeOH (90:10) to afford the title compound as a white solid; m.p. 202°-205° C.

EXAMPLE 3

1-Phenyl-3-acetyl-6-[3-[4-(4-hydroxy)tetrahydropyranyl]benzyloxy]naphthalene

Following the procedure described in Example 1, but substituting 1-phenyl-3-acetyl-6-naphthol (Naphthol 8) for 1-phenyl-3-carbomethoxy-6-naphthol, the title compound was obtained as a white solid. $^1$H NMR (250 MHz, CDCl$_3$): δ1.7 (m, 3H), 2.2 (m, 2H), 2.7 (s, 3H), 3.9 (m, 4H), 5.2 (s, 2H), 7.25 (m, 1H), 7.4–7.5 (m, 10H), 7.65 (s, 1H), 7.85 (m, 2H), 8.35 (s, 1H).

EXAMPLE 4

1-Phenyl-3-[2-(2-hydroxy)propyl]-6-[3-[4-(4-hydroxy)-tetrahydropyranyl]benzyloxy]naphthalene To a solution of the ester from Example 1 (200 mg) in THF (10 mL) at −78° C. was added MeLi in Et$_2$O (1.4M, 1.45 mL) dropwise. The reaction mixture was stirred at −78° C. for 2 hr, then quenched with a saturated NH$_4$Cl solution and diluted with Et$_2$O. The organic phase was separated, washed with H$_2$O, brine, dried over MgSO$_4$ and evaporated. The residue was flash chromatographed on silica gel, eluting with hexane:EtOAc:CH$_2$Cl$_2$ (1:1:1) to afford the title compound as a white foam.

$^1$H NMR (250 MHz, CDCl$_3$): δ1.65–1.75 (m, 3H), 1.7 (s, 6H), 1.9 (s, 0H), 2.2 (m, 2H), 3.9 (m, 4H), 5.2 (s, 2H), 7.15 (dd, 1H), 7.30 (d, 1H), 7.35–7.50 (m, 9H), 7.65 (s, 1H), 7.80 (d, 1H), 7.85 (d, 1H).

EXAMPLE 5

1-Phenyl-3-hydroxymethyl-6-[3-[4-(4-hydroxy)tetrahydropyranyl]benzyloxy]naphthalene To a solution of the ester from Example 1 (500 mg) in THF at −78° C. was added DIBAL-H in toluene (1M, 3.5 mL). The reaction mixture was stirred 1 hr at −78° C., then quenched dropwise with HCl 10% and diluted with Et₂O. The organic phase was separated, washed with HCl 10% (2×), H₂O, brine, dried over MgSO₄ and evaporated. The residue was flash chromatographed on silica gel, eluting with hexane:EtOAc (40:60) to afford the title compound as a white foam.

$^1$H 1.9 (t, 0H), 2.2 (m, 2H), 3.9 (m, 4H), 4.85 (d, 2H), 5.2 (s, 2H), 7.15 (dd, 1H), 7.25 (d, 1H), 7.4–7.5 (m, 9H), 7.65 (s, 1H), 7.7 (s, 1H), 7.8 (d, 1H).

EXAMPLE 6

1-Phenyl-3-methoxymethyl-6-[3-[4-(4-hydroxy)tetrahydropyranyl]benzyloxy]naphthalene To a solution of the alcohol from Example 5 (148 mg) in THF (10 mL) at 0° C. was added aH (10 mg) followed by MeI (30 mL). The reaction mixture was stirred at r.t. for 18 hr, then quenched with saturated H₄Cl solution and diluted with Et₂O. The organic phase was separated, washed with H₂O, brine, dried over MgSO₄ and evaporated. The residue was flash chromatographed on silica gel, eluting with hexane:EtOAc (60:40→50:50) to afford the title compound as a white foam.

$^1$H NMR (250 MHz, CDCl₃): δ1.6 (s, 0H), 1.7 (m, 2H), 2.2 (m, 2H), 3.45 (s, 3H), 3.9 (m, 4H), 4.65 (s, 2H), 5.2 (s, 2H), 7.15 (dd, 1H), 7.25 (m, 1H), 7.4–7.5 (m, 9H), 7.65 (s, 1H), 7.7 (s, 1H), 7.8 (d, 1H).

EXAMPLE 7

1-Phenyl-3-(1-hydroxyethyl)-6-[3-[4-(4-hydroxy)tetrahydropyranyl]benzyloxy]naphthalene To a solution of the acetyl derivative from Example 3 (275 mg) in EtOH (10 mL) was added NaBH₄ (45 mg). The reaction mixture was stirred at r.t. for 3 hr, then quenched dropwise with NaOH 10% and diluted with Et₂O. The organic phase was separated, washed with H₂O, brine, dried over MgSO₄ and evaporated. The residue was treated with Et₂O and filtered to afford the title compound as a white solid; m.p. 138.5°–140.5° C.

EXAMPLE 8

1-Phenyl-3-(1-methoxyethyl)-6-[3-[4-(4-hydroxy)tetrahydropyranyl]benzyloxy]naphthalene Following the procedure described in Example 6, but substituting the alcohol from Example 7 for the alcohol from Example 5, the title compound was obtained as a foam after flash chromatography on silica gel, eluting with hexane:EtOAc:CH₂Cl₂ (3:2:1).

$^1$H NMR (250 MHz, CDCl₃): δ1.55 (d, 3H), 1.7 (s, 0H), 1.75 (m, 2H), 2.2 (m, 2H), 3.3 (s, 3H), 3.9 (m, 4H), 4.45 (q, 1H), 5.2 (s, 2H), 7.15 (dd, 1H), 7.25 (m, 1H), 7.4–7.5 (m, 9H), 7.65 (s, 2H), 7.82 (d, 1H).

EXAMPLE 9

1-Phenyl-3-ethyl-6-[3-[4-(4-hydroxy)tetrahydropyranyl]benzyloxy]naphthalene

Following the procedure described in Example 1, but substituting 1-phenyl-3-ethyl-6-naphthol (Naphthol 10) for 1-phenyl-3-carbomethoxy-6-naphthol, the title compound was obtained as a white solid; m.p. 121°–122.5° C.

EXAMPLE 10

1-Phenyl-3-pentanoyl-6-[3-[4-(4-hydroxy)tetrahydropyranyl]benzyloxy]naphthalene

Following the procedure described in Example 1, but substituting 1-phenyl-3-pentanoyl-6-naphthol (Naphthol 9) for 1-phenyl-3-carbomethoxy-6-naphthol, the title compound was obtained as a white foam.

$^1$H NMR (250 MHz, CDCl₃): δ0.95 (t, 3H), 1.45 (m, 2H), 1.6 (s, 0H), 1.65–1.85 (m, 4H), 2.2 (m, 2H), 3.1 (t, 2H), 3.9 (m, 4H), 5.2 (s, 2H), 7.25 (m, 1H), 7.4–7.5 (m, 9H), 7.65 (s, 1H), 7.85 (m, 2H), 8.38 (s, 1H).

EXAMPLE 11

1-Phenyl-3-dimethylcarboxamido-6-[3-[4-(4-hydroxy)-tetrahydropyranyl]benzyloxy]naphthalene Following the procedure described in Example 1, but substituting 1-phenyl-3-dimethylcarboxamido-6-naphthol (Naphthol 18) for 1-phenyl-3-carbomethoxy-6-naphthol, the title compound was obtained as a white solid.

$^1$H NMR (250 MHz, DMSO-d₆): δ1.55 (m, 2 H), 2.0 (m, 2H), 3.0 (s, 6H), 3.75 (m, 4H), 5.1 (s, OH), 5.25 (s, 2H), 7.2–7.55 (m, 10H), 7.6–7.75 (m, 3H), 7.9 (s, 1H).

EXAMPLE 12

1-Phenyl-3-phenylthiomethyl-6-[3-[4-(4-hydroxy)-tetrahydropyranyl)benzyloxy]napthalene Following the procedure described in Example 1, but substituting 1-phenyl-3-phenylthiomethyl-6-naphthol (Naphthol 17) for 1-phenyl-3-carbomethoxy-6-naphthol, the title compound was obtained as a foam.

$^1$H NMR (250 MHz, CDCl₃); δ1.6–1.7 (m, 2H), 2.2 (m, 2H), 3.9 (m, 4H), 4.3 (s, 2H), 5.2 (s, 2H), 7.2–7.5 (m, 16H), 7.65 (m, 2H), 7.8 (d, 1H).

EXAMPLE 13

1-Phenyl-3-methylthiomethyl-6-[3-[4(4-hydroxy)-tetrahydropyranyl]benzyloxy]naphthalene Step 1: 1-Phenyl-3-chloromethyl-6-[3-[4(4-hydroxy)-tetrahydropyranyl]benzyloxy]naphthalene Following the procedure described in Example 1, but substituting 1-phenyl-3-chloromethyl-6-naphthol (from Naphthol 17, Step 2) for 1-phenyl-3-carbomethoxy-6-naphthol, the title compound was obtained as a cream solid.

Step 2: 1-Phenyl-3-methylthiomethyl-6-[3-[4-(4-hydroxy)tetrahydropyranyl]benzyloxy]naphthalene To a solution of the chloromethyl derivative from Step 1 (250 mg, 0.5 mmoL) in DMF (10 mL) was added (5 eq, 191 mg, 2.7 mmoL) of sodium thiomethoxide. The resulting reaction mixture was stirred at r.t. for 5 hr, then transferred to H₂O and extracted with EtOAc. The organic phase was washed successively with saturated NaHCO₃ solution and brine. After evaporation of the solvents, purification by &,ash chromatography (hexane:EtOAc, 1:1) gave the title compound, as a foam.

$^1$H NMR (250 MHz, CDCl₃): δ1.7 (m, 2H), 2.05 (s, 3H), 2.2 (m, 2H), 3.85 (s, 2H), 3.9 (m, 4H), 5.2 (s, 2H), 7.15 (dd, 1H), 7.25 (m, 2H), 7.45 (m, 8H), 7.65 (d, 2H), 7.8 (d, 1H).

EXAMPLE 14

1-Phenyl-3-cyanomethyl-6-[3-[4-(4-hydroxy)tetrahydropyranyl]benzyloxy]naphthalene To a solution of the chloromethyl derivative from Example 13, Step 1, (300 mg, 0.65 mmoL) in dry DMF (10 mL) was added NaCN (10 eq, 320 mg, 6.5 mmoL). The resulting mixture was stirred at r.t. for 5 hr, then transferred to $H_2O$ and extracted with EtOAc. The organic phase was washed successively with saturated $NaHCO_3$ solution and brine. After evaporation of the solvent, purification by flash chromatography (hexanes:EtOAc/3:2) gave the title compound as a foam.

$^1$H NMR (250 MHz, $CDCl_3$): δ1.65 (m, 2H), 3.9 (m, 6H), 5.2 (s, 2H), 7.2 (dd, 1H), 7.25 (m, 2H), 7.45 (m, 8H), 7.7 (d, 2H), 7.8 (d, 1H).

EXAMPLE 15

1-Phenyl-3-methylthioacetyl-6-[3-[4-(4-hydroxy)-tetrahydropyranyl]benzyloxy]naphthalene Following the procedure described in Example 1, but substituting 1-phenyl-3-methylthioacetyl-6-naphthol (Naphthol 16) for 1-phenyl-3-carbomethoxy-6-naphthol, the title compound was obtained as a light yellow foam.

$^1$H NMR (250 MHz, $CDCl_3$): δ1.6 (s, OH), 1.7 (m, 2H), 2.2 (s, 3H), 2.2 (m, 2H), 3.9 (m, 6H), 5.2 (s, 2H), 7.25 (dd, 1H), 7.4–7.5 (m, 9H), 7.65 (s, 1H), 7.85 (m, 2H), 8.4 (s, 1H)

EXAMPLE 16

1-Phenyl-3-carbomethoxymethoxymethyl-6-[3-[4-(4-hydroxy)tetrahydropyranyl]benzyloxy]naphthalene A mixture of the alcohol from Example 5 (71 mg), methyl bromoacetate (20 mL), $Cs_2CO_3$ (80 mg) in DMF (6 mL) was stirred at r.t. for 3 days. The reaction mixture was diluted with $H_2O$ and $Et_2O$, the organic phase was separated, washed with $H_2O$, brine, dried over $MgSO_4$ and evaporated. The residue was flash chromatographed on silica gel, eluting with hexane:EtOAc (50:50) to afford the title compound as a foam.

$^1$H NMR (300 MHz, $CDCl_3$): δ1.6 (s, OH), 1.7 (m, 2H), 2.22 (m, 2H), 3.78 (s, 3H), 3.9 (m, 4H), 4.68 (s, 2H), 5.2 (s, 2H), 5.4 (s, 1H), 7.2 (dd, 1H), 7.25 (m, 2H), 7.4–7.5 (m, 8H), 7.65 (s, 1H), 7.75 (s, 1H), 7.8 (d, 1H).

EXAMPLE 17

1-Phenyl-3-cyano-6-[3-[4-(4-hydroxy)tetrahydropyranyl]benzyloxy]naphthalene

Following the procedure described in Example 1, but substituting 1-phenyl-3-cyano-6-naphthol (Naphthol 13) for 1-phenyl-3-carbomethoxy-6-naphthol, the title compound was obtained as a foam.

$^1$H NMR (250 MHz, $CDCl_3$) δ1.6–1.7 (dd, 2H), 2.1–2.3 (m, 2H), 3.8–4.0 (m, 4H), 5.2 (s, 2H) and 7.8–8.1 (m, 14H).

EXAMPLE 18

1-(3-Furyl)-3-cyano-6-[3-[4-(4-hydroxy)tetrahydropyranyl]benzyloxy]naphthalene

Following the procedure described in Example 1, but substituting 1-(3-furyl)-3-cyano-6-naphthol (Naphthol 14) for 1-phenyl-3-carbomethoxy-6-naphthol, the title compound was obtained as a cream-colored solid, m.p. 144°–145° C.

EXAMPLE 19

1-(3-Furyl)-3-carbomethoxy-6-[3-[4-(4-hydroxy)tetrahydropyranyl]benzyloxy]naphthalene Following the procedure described in Example 1, but substituting 1-(3-furyl)-3-carbomethoxy-6-naphthol (Naphthol 12) for 1-phenyl-3-carbomethoxy-6-naphthol, the title compound was obtained as a white foam.

$^1$H NMR (300 MHz, $CDCl_3$): δ1.7 (m, 3H), 2.22 (m, 2H), 3.95 (m, 4H), 3.98 (s, 3H), 5.2 (s, 2H), 6.7 (s, 1H), 7.3–7.5 (m, 5H), 7.6 (t, 1H), 7.68 (s, 1H), 7.70 (s, 1H), 7.9 (s, 1H), 8.1 (d, 1H), 8.45 (s, 1H).

EXAMPLE 20

1-(3-Furyl)-3-formyl-6-[3-[4-(4-hydroxy)tetrahydropyranyl]benzyloxy]naphthalene

Following the procedure described in Example 1, but substituting 1-(3-furyl)-3-formyl-6-naphthol (Naphthol 15) for 1-phenyl-3-carbomethoxy-6-naphthol, the title compound was obtained as a yellow foam.

$^1$H NMR (300 MHz, $CDCl_3$): δ1.7 (m, 3H), 2.2 (m, 2H), 3.9 (m, 4H), 5.2 (s, 2H), 6.7 (s, 1H), 7.3–7.5 (m, 5H), 7.6 (t, 1H), 7.65 (s, 1H), 7.7 (s, 1H), 7.8 (d, 1H), 8.12 (d, 1H), 8.2 (s, 1H), 10.15 (s, 1H).

EXAMPLE 21

1-(3-Furyl)-3-cyano-6-[5-[4-(4-hydroxy)tetrahydropyranyl]pyridin-3-ylmethoxy]naphthalene To a mixture of 1-(3-furyl)-3-cyano-6-naphthol (Naphthol 14, 176 mg), 5-[4-(4-hydroxy)tetrahydropyranyl]pyridin-3-yl methanol (Alcohol 5, 157 mg) and triphenylphosphine (236 mg) in THF (8 mL), there was added di-tert-butyl azodicarboxylate (207 mg) and the mixture was stirred at r.t. for 2 hr. After evaporation of the THF, the residue was chromatographed on a column of silica gel, eluting with EtOAc. The product obtained was triturated with a 1:1 mixture of $Et_2O$ and hexane, affording on filtration a solid which was crystallized from EtOAc/hexane to afford the title compound as cream-colored microcrystals; m.p. 176°–178° C.

EXAMPLE 22

[1S, 5R]1-(3-Furyl)-3-cyano-6 [5-[3-(3α-hydroxy-6,8-dioxabicyclo[3.2.1]octanyl)]pyridin-3-ylmethoxy]naphthalene Following the procedure described in Example 21, but substituting [1S, 5R]5-[3-(3α-hydroxy-6, 8-dioxabicyclo[3.2.1]octanyl)]pyridin-3-ylmethanol(Alcohol 9), for 5-[4-(4-hydroxy)tetrahydropyranyl]-pyridin-3-ylmethanol, the title compound was obtained as a yellow solid, m.p. 97° C. (dec).

EXAMPLE 23

[1S, 5R]1-(3-Furyl)-3-cyano-6-[3-[3-(3α-hydroxy-6,8-dioxabicyclo[3.2.1]octanyl)]benzyloxy]naphthalene Following the procedure described in Example 21, but substituting [1S, 5R]3-[3-(3α-hydroxy-6,8-dioxabicyclo[3.2.1]octanyl)]benzyl alcohol (Alcohol 4) for 5-[4-(4-hydroxy)tetrahydropyranyl]pyridin-3-ylmethanol, the title compound was obtained as a foam.

$^1$H NMR (250 MHz, $CDCl_3$): δ2.05 (dd, 2H), 2.3 (d, 1H), 2.5 (dd, 1H), 3.8 (m, 1H), 3.95 (s, 1H), 4.5 (d, 1H), 4.7 (m, 1H), 5.2 (m, 1H), 5.8 (s, 1H), 6.65 (s, 1H), 7.2–7.7 (m, 9H), 8.1 (m, 2H).

EXAMPLE 24

1-(3-Furyl)-3-cyano-6-[2-[4-(4-hydroxy)tetrahydropyranyl[thiazol-4-ylmethoxy]naphthalene Following the procedure described in Example 21, but substituting 2-[4-(4-hydroxy)tetrahydropyranil]-thiazol-4-ylmethanol (Alcohol 6) for 5-[4-(4-hydroxy)-tetrahydropyranyl]pyridin-3-ylmethanol, the title compound was obtained as a cream-colored solid; m.p. 157°–159° C. (dec).

EXAMPLE 25

1-(3-Furyl)-3-cyano-6-[3-[4-(4α-hydroxy-2-methyl)tetrahydropyranyl]benzyloxy]naphthalene Following the procedure described in Example 21, but substituting 3-[4-(4α-hydroxy-2-methyl)tetrahydropyranyl]benzyl alcohol (Alcohol 2) for 5-[4-(4-hydroxy)tetrahydropyranyl]pyridin-3-ylmethanol, the title compound was obtained as a foam.

$^1$H NMR (250 MHz, acetone-$d_6$): δ1.12 (d, 3H), 1.55–1.8 (m, 2H), 1.9–2.1 (m, 3H), 3.75–4.0 (m, 3H), 5.32 (s, 2H), 6.86 (br-s, 1H) and 7.35–8.32 (m, 11H).

EXAMPLE 26

1-(3-Furyl)-3-cyano-6-[3-[4-(4β-hydroxy-2-methyl)tetrahydropyranyl]benzyloxy]naphthalene Following the procedure described in Example 21, but substituting 3-[4-(4β-hydroxy-3-methyl)tetrahydropyranyl]benzyl alcohol (Alcohol 3) for 5-[4-(4-hydroxy)tetrahydropyranyl]pyridin-3-ylmethanol, the title compound was obtained as a foam.

$^1$H NMR (250 MHz, acetone-$d_6$): δ1.6 (dd, 1H), 1.8–1.95 (m, 1H), 2.4 (br-t, 2H), 3.2–3.45 (m, 2H), 3.8–3.92 (m, 1H), 5.31 (s, 2H), 6.85 (br-s, 1H) and 7.3–8.3 (m, 1H).

EXAMPLE 27

1-(3-Furyl)-3-cyano-6-[3-[4-(4β-methoxy-2-methyl)tetrahydropyranyl]benzyloxy]naphthalene To a solution of 1-(3-furyl)-3-cyano-6-[3-[4-(4β-hydroxy-2-methyl)tetrahydropyranyl]benzyloxy]naphthalene (106 mg, 0.24 mmoL) in dry THF (3 mL) at 0° C. was added KH (35% in mineral oil, 138 mg, 1.2 mmoL) in dry THF (1 mL). After 10 min. methyl iodide (171 mg, 1.2 mmoL) was added. The mixture was stirred for 30 min. at 0° C., poured into saturated aqueous NH$_4$Cl and extracted with EtOAc. The combined organic layers were washed with brine, dried over MgSO$_4$ and evaporated. Flash chromatography on silica gel (30% EtOAc in hexane) afforded the title product as a foam.

$^1$H NMR (250 MHz, acetone-$d_6$) δ1.11 (d, 2H), 1.5 (m, 1H), 1.8 (m, 1H), 2.45 (m, 2H), 2.78 (m, 2H), 2.8 (s, 3H), 3.3 (m, 2H), 3.85 (m, 1H), 5.36 (s, 2H), 6.87 (br-s, 1H), 8.3–7.4 (m, 11H).

EXAMPLE 28

[1S, 5R] 1-(3-Furyl)-3-cyano-6-[3-[3-(3α-methoxy-6,8-dioxabicyclo[3.2.1]octanyl)]benzyloxy]naphthalene Following the procedure described in Example 27, but substituting [1S, 5R] 1-(3-furyl)-3-cyano-6-[3-[3-(3α-hydroxy-6,8-dioxabicyclo[3.2.1]octanyl)]benzyloxy]-naphthalene (Example 23) for 1-(3-furyl)-3-cyano-6-[3-[4-(4β-hydroxy-2-methyl)tetrahydropyranyl]benzyloxy]naphthalene, the title compound was obtained as a foam.

$^1$H NMR (250 MHz, CDCl$_3$); δ2.0–2.5 (m, 4H), 3.05 (s, 3H), 3.8 (m, 1H), 4.45 (d, 1H), 4.6 (m, 1H), 5.2 (s, 2H), 5.7 (s, 1H), 6.7 (s, 1H), 7.2–7.7 (m, 9H), 8.1 (m, 2H).

EXAMPLE 29

1-(3-Furyl)-3-cyano-6-[6-[4-(4-hydroxy)tetrahydropyranyl]pyridin-2-ylmethoxy]naphthalene Following the procedure described in Example 21, but substituting 6-[4-(4-hydroxy)tetrahydropyranyl]-pyridin-2-ylmethanol (Alcohol 6) for 5-[4-(4-hydroxy)-tetrahydropyranyl]pyridin-3-ylmethanol, the title compound was obtained as a light yellow solid; m.p. 164°–166° C.

EXAMPLE 30

1-(3-Furyl)-3-cyano-6-[3-[4-(4α-hydroxy-2,6-dimethyl)-tetrahydropyranyl]benzyloxy]naphthalene Following the procedure described in Example 1, but substituting 3-[4-(4α-hydroxy-2,6-dimethyl)tetrahydropyranyl]benzyl bromide (Halide 4), for 3-[4-(4-hydroxy)tetrahydropyranyl]benzyl bromide and substituting 1-(3-furyl)-3-cyano-6-naphthol (Naphthol 14); for 1-phenyl-3-carbomethoxy-6-naphthol, the title compound was obtained as a foam.

$^1$H NMR (250 MHz, acetone-$d_6$): δ1.12 (d, 6H), 1.52–1.75 (m, 4H), 4.0 (m, 2H), 5.31 (s, 2H), 6.86 (br-s, 1H), 7.35–7.55 (m, 4H), 7.56 (s, 1H), 7.66 (br-S, 1H), 7.73 (s, 1H), 7.79 (br-s, 1H), 7.97 (s, 1H), 8.17 (d, 1H) and 8.29 (s, 1H).

EXAMPLE 31

[1S, 5R]1-(2-Thienyl)-3-cyano-6-[3-[3-(3α-hydroxy-6,8-dioxabicyclo[3.2.1]octanyl)]benzyloxy]naphthalene Following the procedure described in Example 21 but substituting [1S, 5R]5-[3-(3α-hydroxy-6,8-dioxabicyclo[3.2.1]octanyl]benzyl alcohol (Alcohol 4) for 5-[4-(4-hydroxy)tetrahydropyranyl]pyridin-3-ylmethanol, and substituting 1-(2-thienyl)-3-cyano-6-naphthol (Naphthol 3) for 1-(3-furyl)-3-cyano-6-naphthol, the title compound was obtained as a white solid.

$^1$H NMR (250 MHz, CDCl$_3$): δ2.05 (m, 2H), 2.3 (m, 2H), 2.5 (dd, 1H), 3.8 (m, 1H), 3.95 (s, 1H), 4.5 (d, 1H), 4.7 (m, 1H), 5.7 (s, 2H), 5.8 (s, 1H), 7.15–7.65 (m, 10H), 8.1 (s, 1H), 8.15 (d, 1H).

EXAMPLE 32

[1S, 5R]1-(3-Thienyl)-3-cyano-6-[3-[3-(3α-hydroxy-6,8-dioxabicyclo[3.2.1]octanyl)]benzyloxy]naphthalene Following the procedure described in Example 21, but substituting [1S, 5R]3-[3-(3α-hydroxy-6,8-dioxabicyclo[3.2.1]octanyl]benzyl alcohol (Alcohol 4) for 5-[4-(4-hydroxy)tetrahydropyranyl]pyridin-3-ylmethanol, and substituting 1-(3-thienyl)-3-cyano-6-naphthol (Naphthol 4) for 1-(3-furyl)-3-cyano-6-naphthol, the title compound was obtained as a white solid; m.p. 108°–112° C.

EXAMPLE 33

[1S, 5R]1-(3-Thienyl)-3-cyano-6-[3-[3-(3α-methoxy-6,8-dioxabicyclo[3.2.1]octanyl)]benzyloxy]naphthalene Following the procedure described in Example 27, but substituting [1S, 5R]1-(3-thienyl)-3-cyano-6-[3-[3-(3α-hydroxy-6,8-dioxabicyclo[3.2.1]octanyl)]benzyloxy]naphthalene (Example 32) for 1-(3-furyl)-3-cyano-6-[3-[4-(4β-hydroxy-2-methyl)tetrahydropyranyl]benzyloxy]naphthalene, the title compound was obtained as a white foam.

$^1$H NMR (250 MHz, CDCl$_3$): δ2.1 (dd, 1H), 2.2 (dd, 1H), 2.3 (dd, 1H), 2.4 (dd, 1H), 3.05 (s, 3H), 3.75 (m, 1H), 4.45 (d, 1H), 4.6 (m, 1H), 5.2 (s, 2H), 5.65 (s, 1H), 7.2-7.5 (m, 10H, 8.0 (d, 1H), 8.05 (s, 1H).

EXAMPLE 34

1-(3-Thienyl)-3-cyano-6-[5-[3-[4-(4-hydroxy)tetrahydropyranyl]pyridin-3-yl]methoxy]naphthalene Following the procedure described in Example 21, but substituting 1-(3-thienyl)-3-cyano-6-naphthol (Naphthol 4) for 1-(3-furyl)-3-cyano-6-naphthol, the title compound was obtained as a white solid; m.p. 174°–177° C.

EXAMPLE 35

1-(3-Thienyl)-3-cyano-6-[3-[4-(4-hydroxy)tetrahydropyranyl]benzyloxy]naphthalene Following the procedure described in Example 1, but substituting 1-(3-thienyl)-3-cyano-6-naphthol (Naphthol 4) for 1-phenyl-3-carbomethoxy-6-naphthol, the title compound was obtained as a white solid; m.p. 132°–135° C.

EXAMPLE 36

[1S, 5R]-1-(3-Thienyl)-3-cyano-6-[5-[3-(3α-hydroxy-6,8-dioxabicyclo[3,2,1]octanyl)]pyridin-3-ylmethoxy]naphthalene Following the procedure described in Example 21, but substituting [1S, 5R]5-[3-(3α-hydroxy-6,8-dioxabicyclo[3.2.1]octanyl)]pyridin-3-ylmethanol (Alcohol 9) for 5-[4-(4-hydroxy)tetrahydropyranyl]pyridin-3-ylmethanol, and substituting 1-(3-thienyl)-3-cyano-6-naphthol (Naphthol 4) for 1-(3-furyl)-3-cyano-6-naphthol, the title compound was obtained as a cream-colored solid; m.p. 89° C. (dec).

EXAMPLE 37

1-(2-Thiazolyl)-3-carbomethoxy-6-[3-[4-(4-hydroxy)tetrahydropyranyl]benzyloxy]naphthalene Following the procedure described in Example 1, but substituting 1-(2-thiazolyl)-3-carbomethoxy-6-naphthol (Naphthol 5) for 1-phenyl-3-carbomethoxy-6-naphthol, the title compound was obtained as a cream-colored solid; m.p. 125°–126° C.

EXAMPLE 38

1-(5-Thiazolyl)-3-carbomethoxy-6-[3-[4-(4-hydroxy)tetrahydropyranyl]benzyloxy]naphthalene Following the procedure described in Example 1, but substituting 1-(5-thiazolyl)-3-carbomethoxy-6-naphthol (Naphthol 6) for 1-phenyl-3-carbomethoxy-6-naphthol, the title compound was obtained as a foam.

$^1$H NMR (250 MHz, CDCl$_3$): δ1.6-1.8 (d, 2H), 2.1-2.3 (m, 2H), 3.8-3.9 (m, 4H), 4.0 (s, 3H), 5.2 (s, 2H), 7.2-7.5 (m, 6H), 7.65 (s, 1H), 8.0 (d, 2H), 8.5 (s, 1H) and 8.9 (s, 1H).

EXAMPLE 39

1-Phenyl-6-[3-[4-(4-hydroxy)tetrahydropyranyl]benzyloxy]naphthalene

Following the procedure described in Example 1, but substituting 1-phenyl-6-naphthol (Naphthol 7) for 1-phenyl-3-carbomethoxy-6-naphthol, the title compound was obtained as a gum.

$^1$H NMR (250 MHz, CDCl$_3$): δ1.59 (s, 1H), 1.66 (m, 2H), 2.22 (m, 2H), 3.92 (m, 4H), 5.21 (s, 2H), 7.15-7.55 (m, 13H), 7.66 (s, 1H), 7.75 (d, 1H), 7.82 (d, 1H).

EXAMPLE 40

1-(3-Furyl)-3-cyano-6-[4-[4-(4-hydroxy)tetrahydropyranyl]pyridin-2-ylmethoxy]naphthalene Following the procedure described in Example 21, but substituting 4-[4-(4-hydroxy)tetrahydropyranyl]pyridin-2-ylmethanol (Alcohol 8) for 5-[4-(4-hydroxy)tetrahydropyranyl]pyridin-3-ylmethanol, the title compound was obtained as a yellow solid, m.p. 144° C. (dec).

EXAMPLE 41

1-(3-Furyl)-3-cyano-6-[4-[4-(4-methoxy)tetrahydropyranyl]pyridin-2-ylmethoxy]naphthalene Following the procedure described in Example 21, but substituting 4-[4-(4-methoxy)tetrahydropyranyl]pyridin-2-ylmethanol (Alcohol 7) for 5-[4-(4-hydroxy)tetrahydropyranyl]pyridin-3-ylmethanol, the title compound was obtained as a white solid; m.p. 154°–156° C.

EXAMPLE 42

[1S,5R]-1-(3-Furyl)-3-cyano-6-{6-[3-(3α-hydroxy-6,8-dioxabicyclo[3.2.1]octanyl)]pyridin-2-ylmethoxy}naphthalene Following the procedure in Example 21 but substituting [1S,5R]-6-[3-(3α-hydroxy-6,8-dioxabicyclo[3.2.1]octanyl)]pyridin-2-ylmethanol (Alcohol 10) for 5-[4-(4-hydroxy)tetrahydropyranyl]pyridin-3-ylmethanol, the title compound was obtained as a cream-colored solid; m.p. 161°–163° C.

EXAMPLE 48

1-(3-Furyl)-3-cyano-6-[2-[4-(4-hydroxy)tetrahydropyranyl]pyridin-4-ylmethoxy]naphthalene Following the procedure described in Example 21, but substituting 6-[2-(4-hydroxy)tetrahydropyranyl]pyridin-4-ylmethanol (Alcohol 11) for 5-[4-(4-hydroxy)tetrahydropyranyl]pyridin-3-ylmethanol, the title compound was obtained as a solid; m.p. 161°–165° C.

EXAMPLE 50

1-(3-Thienyl)-3-cyano-6-[6-[4-(4-hydroxy)tetrahydropyranyl]pyridin-2-ylmethoxy]naphthalene Following the procedure described in Example 21, but substituting 6-[4-(4-hydroxy)tetrahydropyranyl]pyridin-2-ylmethanol (Alcohol 6) for 5-[4-(4-hydroxy)tetrahydropyranyl]pyridin-3-ylmethanol and 1-(3-thienyl)-3-cyano-6-naphthol (Naphthol 4) for 1-(3-furyl)-3-cyano-6-naphthol (Naphthol 14), the title compound was obtained as a solid; m.p. 157°–159° C.

EXAMPLE 52

1-(3-Furyl-3-cyano-6-[3-[4-(2,2-dimethyl-4-ethyl-1,3-dioxalanyl)]benzyloxy]naphthalene Following the procedure described in Example 1, but substituting 3-[4-(2,2-dimethyl-4-ethyl-1,3-dioxalanyl)]-benzyl bromide (Halide 6) for 3-[4-(4-hydroxy)tetrahydropyranyl]benzyl bromide, and 1-(3-furyl)-3-cyano-6-naphthol (Naphthol 14) for 1-phenyl-3-carbomethoxy-6-naphthol, the title compound was obtained as a yellow foam.

$^1$H NMR (300 MHz, CDCl$_3$): δ0.80 (t, 3H), 1.33 (s, 3H), 1.54 (s, 3H), 1.81–1.96 (m, 2H), 4.12 (AB, 2H), 5.22 (s, 2H), 6.67 (t, 1H), 7.26–7.68 (m, 9H), 8.05–8.10 (m, 2H).

EXAMPLE 53

1-(3-Furyl)-2-cyano-6-[3-[4-(4-hydroxy)tetrahydropyranyl]benzyloxy]naphthalene

Following the procedure described in Example 1, but substituting 1-(3-furyl)-2-cyano-6-naphthol (Naphthol 19) for 1-phenyl-3-carbomethoxy-6-naphthol, the title compound was obtained as a foam.

$^1$H NMR (300 MHz, acetone-d$_6$): δ1.65 (m, 2H), 2.1 (m, 2H), 3.8 (m, 4H), 5.3 (s, 2H), 6.81 (m, 1H), 7.3–8.0 (m, 11H).

EXAMPLE 54

[1S,5R]
1-Phenyl-6-carbomethoxy-3-{5-fluoro-3-[3-(3α-hydroxy-6,8-dioxabicyclo[3.2.1]octanyl)]phenoxymethyl}naphthalene Following the procedure described in Example 21, but substituting 1-phenyl-3-hydroxymethyl-6-carbomethoxynaphthalene (Naphthalene 1) for 1-(3-furyl)-3-cyano-6-naphthol (Naphthol 14) and [1S,5R] 5-Fluoro-3-[3-(3α-hydroxy-6,8-dioxabicyclo[3.2.1]octanyl)]-phenol (Alcohol 12) for 5-[4-(4-hydroxy)tetrahydropyranyl]pyridin-3-ylmethanol (Alcohol 5), the title compound is obtained.

EXAMPLE 55

[5R]
1-(3-Furyl)-3-cyano-6-{6-[4-(2,4-dihydroxy)-6-hydroxymethyltetrahydropyranyl]pyridin-2-ylmethoxy}naphthalene To a solution of [1S,5R] 1-(3-furyl)-3-cyano-6-{6-[3-(3α-hydroxy-6,8-dioxabicyclo[3.2.1]octanyl]pyridin-2-ylmethoxy}naphthalene (Example 42) (100 mg) in acetonitrile (5 mL), there was added 12N HCl (0.2 mL) and the resulting solution was stirred at r.t. for 1 hr. There was added 10N aq. NaOH (0.5 mL) and after diluting with EtOAc (10 mL) the mixture was washed three times with brine, dried and evaporated. The crude product was chromatographed on silica gel eluting with EtOAc to afford the product as a cream-colored solid; m.p. dec 92° C. (gas).

EXAMPLE 56

[1S,5R]
1-(3-Thienyl)-3-cyano-6-{6-[3-(3α-hydroxy-6,8-dioxabicyclo[3.2.1]octanyl)]pyridin-2-ylmethoxy}naphthalene Following the procedure described in Example 21, but substituting [1S,5R] 6-[3-(3α-hydroxy-6,8-dioxabicyclo[3.2.1]octanyl)]pyridin-2-ylmethanol (Alcohol 10) for 5-[4-(4-hydroxy)tetrahydropyranyl]pyridin-3-ylmethanol and 1-(3-thienyl)-3-cyano-6-naphthol (Naphthol 4) for 1-(3-furyl-3-cyano-6-naphthol (Naphthol 14), the title compound was obtained as a solid.

$^1$H NMR (300 MHz, CDCl$_3$): δ2.0 (m, 2H), 2.45 (dd, 1H), 2.65 (dd, 1H), 3.9 (t, 1H), 4.65 (d, 1H), 4.75 (bt, 1H), 5.15 (s, 1H), 5.35 (s, 2H), 5.85 (s, 1H), 7.3–7.6 (m, 8H), 7.80 (t, 1H), 8.05 (d, 1H), 8.1 (s, 1H).

EXAMPLE 57

1-(5-Pyrimidinyl)-3-carbomethoxy-6-[3-[4-(4-hydroxy)-tetrahydropyranyl]benzyloxynaphthalene Following the procedure described in Example 1, but substituting 1-(5-pyrimidinyl)-3-carbomethoxy-6-naphthol (Naphthol 21) for 1-phenyl-3-carbomethoxy-6-naphthol (Naphthol 11), the title compound was obtained as a white solid; m.p. 176°–177° C.

EXAMPLE 58

[1S,5R]
1-(3-Furyl)-3-acetyl-6-{6-[3-(3α-hydroxy-6,8-dioxabicyclo[3.2.1]octanyl)]pyridin-2-ylmethoxy}naphthalene Following the procedure described in Example 21, but substituting 1-(3-furyl)-3-acetyl-6-naphthol (Naphthol 20) for 1-(3-furyl)-3-cyano-6-naphthol (Naphthol 14) and [1S,5R] 6-[3-(3α-hydroxy-6,8-dioxabicyclo[3.2.-1]octanyl)]pyridin-2-ylmethanol (Alcohol 10) for 5-[4-(4-hydroxy)tetrahydropyranyl]pyridin-3-ylmethanol, the title compound was obtained as a white solid; m.p. 159°–161° C.

EXAMPLE 59

1-(3-Furyl)-3-N-hydroxyacetamidomethyl-6-[3-[4-(4-hydroxy)tetrahydropyranyl]benzyloxy]naphthalene Step 1: 1-(3-Furyl)-3-hydroxyiminomethyl-6-[3-[4-(4-hydroxy)tetrahydropyranyl]benzyloxy]naphthalene To a solution of 1-(3-furyl)-3-formyl-6-[3-[4-(4-hydroxy)tetrahydropyranyl]benzyloxy]naphthalene (Example 20) (235 mg, 0.55 mmoL) in EtOH (5 mL) containing Et$_3$N (153 μL, 1.1 mmoL) was added hydroxylamine hydrochloride (77 mg, 1.1 mmoL). The resulting reaction mixture was then stirred at r.t. for 16 hr. Then the solvent was evaporated and the residue dissolved in EtOAc, washed with H$_2$O, dried, and the solvent evaporated to give the title compound as a solid.

Step 2: 1-(3-Furyl)-3-N-(O-acetyl)-acetamidomethyl-6-[3-[4-(4-hydroxy)tetrahydropyranyl]benzyloxy]naphthalene To a solution of the oxime (243 mg, 0.55 mmoL) from Step 1 in EtOH (5 mL) was added pyridineborane (130 μL, 1.3 mmoL), cooled to 0° C., and added (0.3 mL) of HCl 12N. After 15 min, the resulting reaction mixture was added to a saturated aqueous solution of sodium bicarbonate, then extracted with EtOAc, dried and the solvent was evaporated. The residue was dissolved in CH$_2$Cl$_2$ (8 mL), cooled to 0° C. and pyridine was added (260 μL, 3.2 mmoL) followed dropwise by acetyl chloride (230 μl, 3.2 mmoL). The reaction mixture was stirred for 30 min, diluted with EtOAc and the organic phase was washed successively with HCl 1N, brine and evaporated. The residue was flash chromatographed using (hexane:EtOAc, 7:3) to give of the title compound as a solid.

Step 3: 1-(3-Furyl-3-N-hydroxyacetamidomethyl-6-[3-[4-(4-hydroxy)tetrahydropyranyl]benzyloxy]naphthalene To a solution of the diacetate from Step 2 (200 mg, 0.38 mmoL) in MeOH (10 mL) was added $K_2CO_3$ (16 mg, 0.12 mmoL) at r.t. After 15 min, the reaction mixture was added to HCl 1N, extracted with EtOAc. The combined organic phases were washed successively with $H_2O$ brine, dried, and evaporated to give, after purification by flash chromatography ($CH_2Cl_2$:MeOH, 98:2), the title compound as a white solid.

$^1$H NMR (300 MHz, $CDCl_3$): δ1.6 (m, 2H), 2.2 (bs, 5H), 3.9 (m, 4H), 4.9 (s, 2H), 5.15 (s, 2H), 6.65 (d, 1H), 7.2 (m, 3H), 7.45 (m, 3H), 7.6 (m, 4H), 8.0 (d, 1H).

EXAMPLE 60

1-(Tetrazol-5-yl)-3-carbomethoxy-6-[3-[4-(4-hydroxy)-tetrahydropyranyl]benzyloxy]naphthalene Step 1: 1-Cyano-3-carbomethoxy-6-[3-[4-(4-hydroxy)tetrahydropyranyl]benzyloxy]naphthalene Following the procedure described in Example 1 but substituting 1-cyano-3-carbomethoxy-6-naphthol (Naphthol 22) for 1-phenyl-3-carbomethoxy-6-naphthol (Naphthol 11), the title compound was obtained as a yellow solid.

Step 2: 1-(Tetrazol-5-yl)-3-carbomethoxy-6-[3-[4-(4-hydroxy)tetrahydropyranyl]benzyloxy]naphthalene To a solution of the cyano intermediate from Step 1 (87 mg, 0.21 mmoL) in 1,2-dichlorobenzene (1.2 mL) was added $Bu_3SnN_3$ (243 mg, 0.63 mmoL) and the resulting mixture was heated at 150° C. for 1.5 hr. Then AcOH (0.1 mL) was added and the reaction mixture was stirred 0.5 hr. Hexane was then added and the heterogenous mixture was filtered and the solvent evaporated to give a yellow solid which was flash chromatographed using (Hexane:EtOAc 1:1→MeOH:$CH_2Cl_2$:AcOH 95:5:0.5) to afford the title compound as a yellow solid; m.p. 153°–154° C.

EXAMPLE 61

1-(2-Methyltetrazol-5-yl)-3-carbomethoxy-6-[3-[4-(4-hydroxy)tetrahydropyranyl]benzyloxy]naphthalene Following the procedure described in Naphthol 5, Step 8, but substituting 1-(tetrazol-5-yl)-3-carbomethoxy-6-[3-[4-(4-hydroxy)tetrahydropyranyl]benzyloxy]naphthalene from Example 60 for 1-(2-thiazolyl)-3-carboxy-6-naphthol, the title compound was obtained as a yellow solid; m.p. 140°–143° C.

EXAMPLE 70

1-Phenyl-6-carbomethoxy-3-[5-fluoro-3-[4-(4-methoxy)tetrahydropyranyl]phenoxymethyl]naphthalene Following the procedure described in Example 21, but substituting 1-phenyl-3-hydroxymethyl-6-carbomethoxynaphthalene (Naphthalene 1) for 1-(3-furyl)-3-cyano-6-naphthol (Naphthol 14) and 5-fluoro-3-[4-(4-methoxy)tetrahydropyranyl]phenol (EP 385,662) for 5-[4-(4-hydroxy)tetrahydropyranyl]pyridin-3-ylmethanol (Alcohol 5), the title compound was obtained as a solid.

$^1$H NMR (300 MHz, $CDCl_3$): δ1.95 (m, 4H), 2.95 (s, 3H), 3.8 (m, 4H), 4.0 (s, 3H), 5.25 (s, 2H), 6.7 (m, 2H), 6.85 (m, 1H), 7.5 (m, 5H), 7.6 (d, 1H), 8.0 (m, 3H), 8.65 (d, 1H).

What is claimed is:

1. A compound of the Formula:

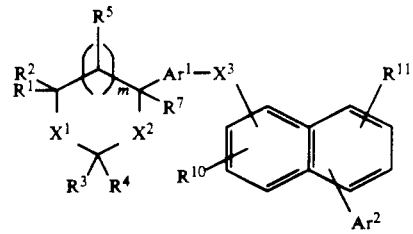

wherein:
$R^1$ and $R^5$ is each independently H, OH, lower alkyl, or lower alkoxy;
$R^2$ is H, lower alkyl, or together with $R^1$ forms a double bonded oxygen (=O);
$R^3$ is H, lower alkyl, hydroxy lower alkyl, or lower alkoxy lower alkyl, or $R^1$ and $R^3$ may join to form a mono-oxa, mono-carbon bridge;
$R^4$ is H or lower alkyl;
$R^6$ is H or lower alkyl;
$R^7$ is H, OH, lower alkyl, lower alkoxy, lower alkylthio, lower alkylcarbonyloxy, or O—$R^{15}$;
$R^8$ is H, halogen, lower alkyl, hydroxy, lower alkoxy, $CF_3$, CN, or $COR^{13}$;
$R^9$ is H, lower alkyl, lower alkoxy, hydroxy lower alkyl, lower alkoxy lower alkyl, lower alkylthio lower alkyl, $(R^8)_2$-phenylthio lower alkyl, lower alkylthio lower alkylcarbonyl, CN, $NO_2$, $CF_3$, $N_3$, $N(R^{12})_2$, $NR^{12}COR^{13}$, $NR^{12}CON(R^{12})_2$, $SR^{14}$, $S(O)R^{14}$, $S(O)_2R^{14}$, $S(O)_2N(R^{12})_2$, $COR^{13}$, $CON(R^{12})_2$, $CO_2R^{13}$, $C(R^{13})_2OC(CR^{13})_2$—$CO_2R^{13}$, $C(R^{13})_2CN$, or halogen;
$R^{10}$ and $R^{11}$ is each independently H, lower alkyl, lower alkoxy, hydroxy lower alkyl, lower alkoxy, lower alkyl, lower alkylthio lower alkyl, $(R^8)_2$-phenylthio lower alkyl, lower alkylthio lower alkylcarbonyl, CN, $NO_2$, $CF_3$, $N_3$, $N(R^{16})_2$, $NR^{16}COR^{13}$, $NR^{16}CON(R^{16})_2$, $SR^{14}$, $S(O)R^{14}$, $S(O)_2R^{14}$, $S(O)_2N(R^{16})_2$, $COR^{13}$, $CON(R^{16})_2$, $CO_2R^{13}$, $C(R^{13})_2OC(CR^{13})_2$—$CO_2R^{13}$, $C(R^{13})_2CN$, halogen, $C(R^{13})_2NR^{16}COR^{13}$, or $C(R^{13})_2NR^{16}CON(R^{13})_2$;
$R^{12}$ is H or lower alkyl, or two $R^{12}$ groups attached to the same nitrogen may form a saturated ring of 5 or 6 members, optionally containing a second heteroatom chosen from O, S or $NR^4$;
$R^{13}$ is H or lower alkyl;
$R^{14}$ is lower alkyl, $CF_3$, or phenyl-$(R^8)_2$;
$R^{15}$ is carboxy lower alkylcarbonyl, pyridylcarbonyl, hydroxy lower alkylcarbonyl, polyoxa lower alkylcarbonyl, a functionalized or unfunctionalized derivative of a standard amino acid, or a benzoyl group substituted by $CH_2N(R^{12})_2$;
$R^{16}$ is H, lower alkyl, or $OR^{13}$;
$X^1$ is O, or $C(R^6)_2$;
$X^2$ is O, or $(CR^6)_2$;
one but not both of $X^1$ or $X^2$ is O;
$X^3$ is $C(R^6)_2O$ or $OC(R^6)_2$;
$Ar^1$ is arylene-$(R^8)_2$, wherein arylene is phenylene, pyridylene or thiazylene;
$Ar^2$ is aryl-$(R^9)_2$ wherein aryl is a 5-membered aromatic ring wherein one carbon atom is replaced by O or S and 0–3 carbon atoms are replaced by N; a 5-membered aromatic ring wherein 1–4 carbon atoms are replaced by N; a 6-membered aromatic ring wherein 0–3 carbon atoms are replaced by N;

2- or 4-pyranone; 2- or 4-pyridinone; or a bicyclic 8-, 9-, or 10-membered aromatic ring wherein 0-2 carbon atoms are replaced by either O or S or a combination thereof and 0-3 carbon atoms are replaced by N; with the proviso that $Ar^2$ is not phenyl when $X^3$ is $OC(R^6)_2$, $Ar^1$ is thiazylene, and $R^7$ is lower alkoxy; with the further proviso that $Ar^2$ is not phenyl when $X^3$ is $OC(R^6)_2$, and $Ar^1$ is phenylene or pyridylene;

$Ar^2$ is attached to either ring of the naphthalene ring system;

m is 1;

p is 0 to 6; and q is 1 or 2;

or a pharmaceutically acceptable salt thereof.

2. A compound of claim 1 of the Formula:

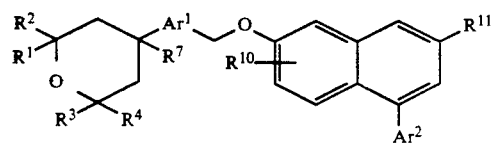

Ia wherein $R^{10}$ is H, lower alkyl, or halogen.

3. A compound of the Formula:

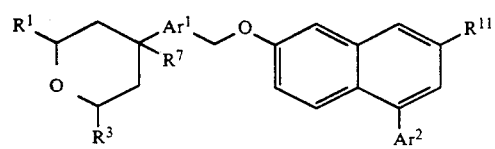

Ib wherein:

$R^1$ and $R^3$ is each independently H or $CH_3$ or together are $-CH_2O-$ or $-OCH_2$;

$R^7$ is OH or $OCH_3$;

$Ar^1$ is Phe, 5,3-Pye, 2,4-Tze, 6,2-Pye, 4,2-Pye, or 2,4-Pye;

$Ar^2$ is Ph, 3-Fu, 2-Th, 3-Th, 2-Tz, 5-Tz, 5-Pym, or 5-Tet;

$R^{11}$ is $CO_2CH_3$, $C(OH)(CH_3)_2$, $CH(OH)CH_3$, $CH(OCH_3)CH_3$, $CH_2CH_3$, $CO(CH_2)_3CH_3$, $CON(CH_3)_2$, $CH_2SC_6H_5$, $CH_2SCH_3$, $CH_2CN$, $COCH_2SCH_3$, $CH_2OCH_2CO_2CH_3$, CN, CHO, H, $COCH_3$, or $CH_2N(OH)COCH_3$.

4. A compound of the Formula:

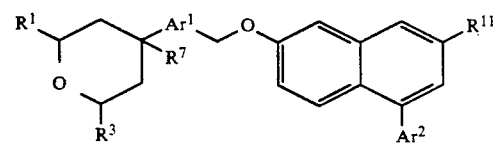

Ib wherein the substituents are as follows:

| [EX.] | $R^1$ | $R^3$ | $R^7$ | $Ar^1$ | $Ar^2$ | $R^{11}$ |
|---|---|---|---|---|---|---|
| [1] | H | H | OH | Phe | Ph | CN |
| [2] | H | H | OH | Phe | Ph | $CO_2H$ |
| [3] | H | H | OH | Phe | Ph | COMe |
| [4] | H | H | OH | Phe | Ph | $C(OH)Me_2$ |
| [5] | H | H | OH | Phe | Ph | $CH_2OH$ |
| [6] | H | H | OH | Phe | Ph | $CH_2OMe$ |
| [7] | H | H | OH | Phe | Ph | CH(OH)Me |
| [8] | H | H | OH | Phe | Ph | CH(OMe)Me |
| [9] | H | H | OH | Phe | Ph | Et |
| [10] | H | H | OH | Phe | Ph | COBu |

-continued

| [EX.] | $R^1$ | $R^3$ | $R^7$ | $Ar^1$ | $Ar^2$ | $R^{11}$ |
|---|---|---|---|---|---|---|
| [11] | H | H | OH | Phe | Ph | $CONMe_2$ |
| [12] | H | H | OH | Phe | Ph | $CH_2SPh$ |
| [13] | H | H | OH | Phe | Ph | $CH_2SMe$ |
| [14] | H | H | OH | Phe | Ph | $CH_2CN$ |
| [15] | H | H | OH | Phe | Ph | $COCH_2SMe$ |
| [16] | H | H | OH | Phe | Ph | $CH_2OCH_2CO_2Me$ |
| [17] | H | H | OH | Phe | Ph | CN |
| [18] | H | H | OH | Phe | 3-Fu | CN |
| [19] | H | H | OH | Phe | 3-Fu | $CO_2Me$ |
| [20] | H | H | OH | Phe | 3-Fu | CHO |
| [21] | H | H | OH | 5,3-Pye | 3-Fu | CN |
| [22] | | $-CH_2O-$ | OH | 5,3-Pye | 3-Fu | CN |
| [23] | | $-CH_2O-$ | OH | Phe | 3-Fu | CN |
| [24] | H | H | OH | 2,4-Tze | 3-Fu | CN |
| [25]* | Me | H | OH | Phe | 3-Fu | CN |
| [26]** | Me | H | OH | Phe | 3-Fu | CN |
| [27]** | Me | H | OMe | Phe | 3-Fu | CN |
| [28] | | $-CH_2O-$ | OMe | Phe | 3-Fu | CN |
| [29] | H | H | OH | 6,2-Pye | 3-Fu | CN |
| [30]* | Me | Me | OH | Phe | 3-Fu | CN |
| [31] | | $-CH_2O-$ | OH | Phe | 2-Th | CN |
| [32] | | $-CH_2O-$ | OH | Phe | 3-Th | CN |
| [33] | | $-CH_2O-$ | OMe | Phe | 3-Th | CN |
| [34] | H | H | OH | 5,3-Pye | 3-Th | CN |
| [35] | H | H | OH | Phe | 3-Th | CN |
| [36] | | $-CH_2O-$ | OH | 5,3-Pye | 3-Th | CN |
| [37] | H | H | OH | Phe | 2-Tz | $CO_2Me$ |
| [38] | H | H | OH | Phe | 5-Tz | $CO_2Me$ |
| [39] | H | H | OH | Phe | Ph | H |
| [40] | H | H | OH | 4,2-Pye | 3-Fu | CN |
| [41] | H | H | OMe | 6,2-Pye | 3-Fu | CN |
| [42] | | $-CH_2O-$ | OH | 6,2-Pye | 3-Fu | CN |
| [43] | | $-CH_2O-$ | OMe | 6,2-Pye | 3-Fu | CN |
| [44] | | $-CH_2O-$ | OH | 4,2-Pye | 3-Fu | CN |
| [45] | | $-CH_2O-$ | OMe | 4,2-Pye | 3-Fu | CN |
| [46] | | $-CH_2O-$ | OH | 2,4-Pye | 3-Fu | CN |
| [47] | | $-CH_2O-$ | OMe | 2,4-Pye | 3-Fu | CN |
| [48] | H | H | OH | 2,4-Pye | 3-Fu | CN |
| [49] | H | H | OMe | 2,4-Pye | 3-Fu | CN |
| [50] | H | H | OH | 6,2-Pye | 3-Th | CN |
| [51] | H | H | OH | 2,4-Pye | 3-Th | CN |
| [55] | $CH_2OH$ | OH | OH | 6,2-Pye | 3-Fu | CN |
| [56] | | $-CH_2O-$ | OH | 6,2-Pye | 3-Th | CN |
| [57] | H | H | OH | PHe | 5-Pym | $CO_2Me$ |
| [58] | | $-CH_2O-$ | OH | 6,2-Pye | 3-Fu | COMe |
| [59] | H | H | OH | Ph | 3-Fu | $CH_2N(OH)COMe$ |
| [60] | H | H | OH | Ph | Tet | $CO_2Me$ |
| [61] | H | H | OH | Ph | 2-MeTet | $CO_2Me$ |
| [72] | | $-CH_2O-$ | OH | 6,2-Pye | 3-Fu | CN |

*α isomer
**β iosmer

5. A compound of the Formula:

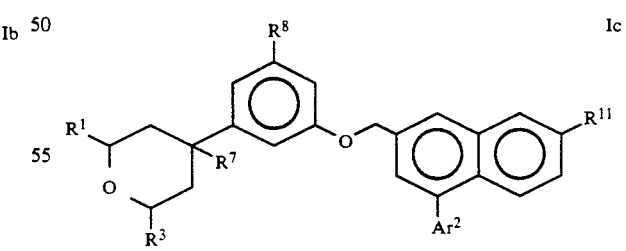

Ic wherein the substituents are as follows:

| [EX.] | $R^1$ | $R^3$ | $R^7$ | $R^8$ | $Ar^2$ | $R^{11}$ |
|---|---|---|---|---|---|---|
| [63] | | $-CH_2O-$ | OH | F | 3-Fu | $CO_2Me$ |
| [64] | | $-CH_2O-$ | OH | F | 3-Fu | CN |
| [65] | | $-CH_2O-$ | OMe | F | 3-Fu | CN |
| [66] | | $-CH_2O-$ | OMe | H | 3-Fu | CN |
| [67] | | $-CH_2O-$ | OMe | F | 3-Th | CN |
| [68] | H | H | OMe | F | 3-Fu | CN |

| [EX.] | R¹ | R³ | R⁷ | R⁸ | Ar² | R¹¹ |
|---|---|---|---|---|---|---|
| [69] | H | H | OMe | F | 3-Th | CN |

6. A compound of the Formula:

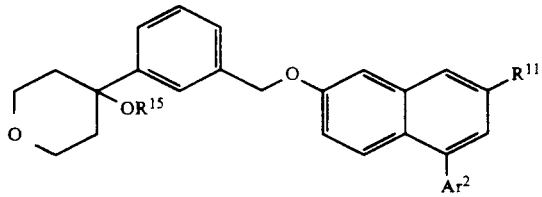

Id wherein the substituents are as follows:

| R¹⁵ | Ar² | R¹¹ |
|---|---|---|
| —CO(CH₂)₂CO₂H | Ph | COCH₃ |
| —CO(CH₂)₂CO₂H | Ph | CN |
| —CO(CH₂)₂CO₂H | Ph | CN |
| —CO-3-Py | Ph | CN |
| —CO(CH₂)₂CO₂Me | Ph | CN |
| —COCH₂NH₂ | Ph | CN |
| —COCH₂OH | 3-Fu | CN |
| —COCH₂NH₂ | 3-Fu | CN |
| —COCH₂NMe₂ | 3-Fu | CN |
| —COCH₂NMe₂ | Ph | CN |
| —COCH₂NHMe | 3-Fu | CN |
| —COCH(NH₂)CH₂CO₂Me | 3-Fu | CN |
| —COCH(NHt-BOC)CH₂CO₂H | 3-Fu | CN |

7. The compound [1S, 5R]-1-(3-Furyl)-3-cyano-6-{6-[3-(3α-hydroxy-6,8-dioxabicyclo[3.2.1]octanyl)]pyridin-2-ylmethoxy}naphthalene.

8. A pharmaceutical composition comprising a therapeutically effective amount of a compound of claim 1 and a pharmaceutically acceptable carrier.

9. The pharmaceutical composition of claim 8 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; H₁- or H₂-receptor antagonists; antihistaminic agents; prostaglandin antagonists; and ACE antagonists.

10. A pharmaceutical composition according to claim 7, wherein the second active ingredient is a non-steroidal anti-inflammatory drug.

11. A pharmaceutical composition of claim 10, wherein the weight ratio of said compound of claim 1 to said second active ingredient ranges from about 1000:1 to 1:1000.

* * * * *